United States Patent [19]
Keana et al.

[11] Patent Number: 5,385,946
[45] Date of Patent: Jan. 31, 1995

[54] METHOD FOR TREATING HYPERTENSION WITH DISUBSTITUTED GRANIDINE COMPOUNDS

[75] Inventors: John Keana, Eugene; Eckard Weber, Portland, both of Oreg.

[73] Assignee: State of Oregon, acting by and through the Oregon State Board of Higher Education, acting for and on behalf of the Oregon Health Sciences University and the University of Oregon, Eugene, Oreg.

[21] Appl. No.: 47,551

[22] Filed: Feb. 23, 1993

Related U.S. Application Data

[60] Division of Ser. No. 528,216, May 25, 1990, abandoned, which is a continuation-in-part of Ser. No. 254,068, Oct. 6, 1988, abandoned, which is a continuation-in-part of Ser. No. 884,150, Jul. 10, 1986, Pat. No. 4,709,094, and a continuation-in-part of Ser. No. 346,494, May 2, 1989, abandoned.

[51] Int. Cl.⁶ .......................................... A61K 31/155
[52] U.S. Cl. ................................................. 514/634
[58] Field of Search ........................................ 514/634

[56] References Cited

U.S. PATENT DOCUMENTS

| | | | |
|---|---|---|---|
| 1,422,506 | 7/1922 | Weiss | 564/238 |
| 1,597,233 | 8/1926 | Heuser et al. | 564/238 |
| 1,642,180 | 9/1927 | Scott | 564/238 |
| 1,672,431 | 6/1928 | Schotte | 514/634 |
| 1,756,315 | 4/1930 | Ter Horst | 564/238 |
| 1,795,738 | 3/1931 | Schotte | 514/634 |
| 1,850,682 | 3/1932 | Meiss | 564/238 |
| 1,915,922 | 6/1933 | Christman et al. | 514/634 |
| 2,145,214 | 1/1939 | Jayne, Jr. | 514/634 |
| 2,254,009 | 8/1941 | Hechenbleikner | 564/238 |
| 2,274,476 | 2/1942 | Hechenbleikner | 564/238 |
| 2,362,915 | 11/1944 | MacGregor | 564/238 |
| 2,633,474 | 3/1953 | Beaver | 564/238 |
| 3,140,231 | 7/1964 | Luskin et al. | 514/634 |
| 3,159,676 | 12/1964 | Spickett et al. | 564/238 |
| 3,228,975 | 1/1966 | Abraham et al. | 514/634 |
| 3,248,426 | 4/1966 | Dvornik | 514/634 |
| 3,270,054 | 8/1966 | Gagneux et al. | 564/238 |
| 3,283,003 | 11/1966 | Jack et al. | 514/634 |
| 3,301,755 | 1/1967 | Mull | 564/238 |
| 3,320,229 | 5/1967 | Szabo et al. | 564/238 |
| 3,409,669 | 11/1968 | Dyke | 564/238 |

(List continued on next page.)

FOREIGN PATENT DOCUMENTS

| | | |
|---|---|---|
| 0001500 | 4/1979 | European Pat. Off. . |
| 0035374 | 9/1981 | European Pat. Off. . |
| 0179642 | 4/1986 | European Pat. Off. . |
| 514248 | 9/1927 | Germany . |
| 2133056 | 1/1973 | Germany . |
| 2916140 | 10/1979 | Germany . |
| 223410 | 10/1924 | United Kingdom . |
| 258203 | 9/1926 | United Kingdom . |
| 478515 | 1/1938 | United Kingdom . |
| WO87/04433 | 7/1987 | WIPO . |
| WO88/00583 | 1/1988 | WIPO . |
| WO90/14067 | 11/1990 | WIPO . |
| WO92/14697 | 9/1992 | WIPO . |

*Primary Examiner*—Raymond J. Henley, III
*Attorney, Agent, or Firm*—David G. Conlin; Peter F. Corless

[57] ABSTRACT

N,N-disubstituted-guanidines, e.g., of the formula

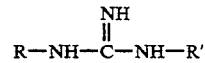

wherein R and R' are substituted or unsubstituted hydrocarbon groups.

Methods are provided for the treatment of psychosis and hypertension by administering an effective amount of an N,N'-disubstituted guanidine which, preferably, has a high affinity for the sigma receptor.

26 Claims, No Drawings

U.S. PATENT DOCUMENTS

| | | | |
|---|---|---|---|
| 3,479,437 | 11/1969 | Szabo et al. | 514/634 |
| 3,547,951 | 12/1970 | Hardie et al. | 514/634 |
| 3,639,477 | 2/1972 | L'Ltalien | 564/238 |
| 3,681,459 | 8/1972 | Hughes et al. | 564/238 |
| 3,769,427 | 10/1973 | Hughes et al. | 514/634 |
| 3,804,898 | 4/1974 | Panneman | 514/634 |
| 3,908,013 | 9/1975 | Hughes et al. | 564/238 |
| 3,968,243 | 7/1976 | Maxwell et al. | 514/634 |
| 3,976,643 | 8/1976 | Diamond et al. | 514/634 |
| 3,976,787 | 8/1976 | Hughes et al. | 564/238 |
| 4,007,181 | 2/1977 | DuCharme et al. | 564/238 |
| 4,014,934 | 3/1977 | Hughes et al. | 564/238 |
| 4,051,256 | 9/1977 | Swallow | 564/238 |
| 4,052,455 | 10/1977 | Matier et al. | 564/238 |
| 4,109,014 | 8/1978 | Liu et al. | 564/238 |
| 4,130,663 | 12/1978 | Matier et al. | 514/634 |
| 4,169,154 | 9/1979 | Cohen et al. | 514/634 |
| 4,284,642 | 8/1981 | Toldy et al. | 424/273 |
| 4,369,325 | 1/1983 | Toldy et al. | 548/315 |
| 4,471,137 | 9/1984 | Barton et al. | 514/634 |
| 4,575,514 | 3/1986 | Carson | 564/238 |
| 4,709,094 | 11/1987 | Weber et al. | 514/634 |
| 4,780,466 | 10/1988 | Hrib et al. | 514/634 |
| 4,898,978 | 2/1990 | Bergfeld et al. | 564/238 |
| 4,906,779 | 3/1990 | Weber et al. | 564/238 |
| 5,093,525 | 3/1992 | Weber et al. | 564/238 |
| 5,190,976 | 3/1993 | Weber et al. | 514/634 |

OTHER PUBLICATIONS

S. Siddiqui et al., *Pakistan Journal of Scientific and Industrial Research*, 30(3):163–181 (1987).

C. Chavkin et al., *Advances in the Biosciences*, 75:407–410 (1989).

J. Keana et al., *Proc. Natl. Acad. Sci. U.S.A.*, 86:5631–5635 (1989).

H. Wanzlick et al., *Chemische Berichte*, 98(10):3170–3177 (1965).

D. Lloyd et al., *Tetrahedron*, 33:1379–1389 (1977).

K. Akiba et al., *Bulletin of the Chem. Soc. of Japan*, 47(4):935–937 (1974).

Database Rtecs, No. MF735000 (1990).

E. Maida et al., *Wiener Klinische Wochenschrift*, 90(1):43–48 (1978).

H. Shimizu, *Chem. Abstracts*, 111(2), Abstr. No. 16337m (1989).

A. Heesing et al., *Chem. Abstracts*, 64(11), Abstr. No. 15776h (1966).

T. Tada et al., *Chem. Abstracts*, 104(24), Abstr. No. 208252g (1986).

L. Kiselev et al., *Chem. Abstracts*, 91(21), Abstr. No. 175291b (1979).

F. Monnet et al., "Multiple Sigma and PCP Receptor Ligands: Mechanism For Neuromodulation and Protection", (1991).

A. Wilson et al., *J. Nuclear. Medicine*, 31(5):747, abstract No. 376 (1990).

B. Cambell et al., *European Journal of Pharmacology*, 205:219–233 (1991).

T. Massamiri et al., *The Journal of Pharmacology and Experimental Therapeutics*, 259(1):22–29 (1991).

J. T. Adams et al., *Eur. J. Pharm.*, 142:61–71 (1987).

P. N. Bhargava et al., *Chemical Abstracts*, 86:598, 189787b (1977).

W. D. Bowen et al., *Eur. J. Pharm.*, 147:153–154 (1988).

B. G. Campbell et al., *J. Neurosci.*, 9(10):3380–3391 (1989).

I. V. Dranka et al., *Russian J. Inorg. Chem.*, 26(3):347–350 (1981).

G. J. Durant et al., *J. Med. Chem.*, 28:1414–1422 (1985).

S. E. File, *TINS*, 10:461–463 (1987).

H. W. Geluk et al., *J. Med. Chem.*, 17:712–715 (1969).

M. P. Kavanaugh et al., *Proc. Natl. Acad. Sci. USA*, 85:2844–2848 (1988).

C. A. Maryanoff et al., *J. Org. Chem.*, 51:1882–1884 (1986).

S. R. Safir et al., *J. Org. Chem.*, 13:924–932 (1948).

M. W. Scherz et al., *J. Med. Chem.*, 33:2421–2429 (1990).

M. S. Sonders et al., *TINS*, 11:37–40 (1988).

A. A. Stolyarchuk et al., *Chemical Abstracts*, 86:522–523, 121071h (1977).

B. Tester et al., *Society for Neuroscience, 19th Annual Meeting*, p. 983, 396.17 (1989).

T. J. R. Weakley et al., *Acta Cryst.*, 46:2234–2236 (1990).

E. Weber et al., *Proc. Natl. Acad. Sci. U.S.A.*, 83:8784–8788 (1986).

H. G. M. Westenberg et al., *Psychopharmacol. Bull.*, 23:145–149 (1987).

Supplementary Partial European Search Report for the corresponding European Application No. EP 8790447.

International Search Report for International Application No. PCT/US90/02398, filed May 2, 1990.

METHOD FOR TREATING HYPERTENSION WITH DISUBSTITUTED GRANIDINE COMPOUNDS

The government has certain rights in this invention pursuant to Grant No. MH 40303 awarded by the National Institutes of Health.

CROSS REFERENCE TO RELATED APPLICATIONS

This is a division of copending application Ser. No. 07/528,216 filed on May 25, 1990 now abandoned, which is a continuation-in-part of U.S. application Ser. No. 07/254,068, filed Oct. 6, 1988 now abandoned; which is a continuation-in-part of PCT Application No. PCT/US87/01545, filed Jun. 26, 1987; which is a continuation-in-part of U.S. application Ser. No. 06/884,150 filed Jul. 10, 1986, now U.S. Pat. No. 4,709,094, the disclosures of which are fully incorporated by reference herein. The present application is also a continuation-in-part of U.S. application Ser. No. 07/346,494, filed May 2, 1989 now abandoned, the disclosure of which is fully incorporated by reference herein.

FIELD OF THE INVENTION

The invention is in the field of medicinal chemistry. In particular, the invention relates to substituted guanidines which bind to the sigma receptor and pharmaceutical compositions thereof which are useful for the treatment of psychotic mental illness and hypertension in animals.

BACKGROUND OF THE INVENTION

Recently, the inventors have described a series of di-aryl-guanidines which are potent ligands for brain sigma receptors (Weber, et al., *PNAS (USA)* 83:8784–8788 (1986); Campbell et al., *J. Neurosci,* 9:3380–3391 (1989); U.S. Pat. No. 4,709,094). Brain sigma receptors bind many psychotropic drugs (Sonders et al., *Trends Neurosci.* 11:37–40 (1988)). The physiological function of sigma receptors in the nervous system is subject to intense investigations (Sonders et al., *Trends Neurosci.* 11:37–40 (1988)) because certain sigma receptor selective compounds have known antipsychotic activity suggesting that sigma receptor active compounds can be used for the treatment of schizophrenia (Largent et al., *Eur. J. Pharmacol.* 11:345–347 (1988)).

A wide variety of substituted guanidines are disclosed in the patent literature. For example:

U.S. Pat. No. 1,411,731 and 1,422,506 discloses diphenylguanidine as a rubber accelerator;

U.S. Pat. No. 1,597,233 discloses N-o-tolyl-N'-phenyl-guanidine as a rubber accelerator;

U.S. Pat. No. 1,672,431 discloses N,N'-di-o-methoxyphenyl-guanidine as being useful for therapeutic purposes, especially in the form of water-soluble salts;

U.S. Pat. No. 1,730,338 discloses N-p-dimethylamino-phenyl-N'-phenylguanidine as a rubber accelerator;

U.S. Pat. No. 1,795,738 discloses a process for the production of N,N'-dialkyl-di-substituted guanidines, including N-di-ethyl-N'-phenyl-guanidine, N-diethyl-N-isoamylguanidine, N-dimethyl-N'-isoamylguanidine and N-dimethyl-N'-ethylguanidine;

U.S. Pat. No. 1,850,682 discloses a process for the preparation of disubstituted guanidine rubber accelerators bearing an additional substituent on the imine nitrogen atom;

U.S. Pat. No. 2,145,214 discloses the use of disubstituted guanidines, e.g., diarylguanidines especially dixylylguanidine, as parasiticides;

U.S. Pat. No. 2,254,009 discloses sym-di-2-octyl-guanidine and U.S. Pat. Nos. 2,274,476 and 2,289,542 disclose sym-dicyclohexylguanidine as insecticides and moth larvae repellents;

U.S. Pat. No. 2,633,474 discloses 1,3-bis(o-ethylphenyl)guanidine and 1,3-bis(p-ethylphenyl)guanidine as rubber accelerators;

U.S. Pat. No. 3,117,994 discloses N,N',N''-trisubstituted guanidines and their salts as bacteriostatic compounds;

U.S. Pat. No. 3,140,231 discloses N-methyl- and N-ethyl-N'-octylguanidines and their salts as antihypertensive agents;

U.S. Pat. No. 3,248,246 describes (Example 5) a 1,3-disubstituted guanidine whose substituents are hydrophobic hydrocarbon groups, one of which is naphthylmethyl and the other is n-butyl;

U.S. Pat. No. 3,252,816 discloses various N-substituted and unsubstituted cinnamyl-guanidines and generically the corresponding N'- and N''-alkyl substituted compounds and their salts as antihypertensive agents;

U.S. Pat. No. 3,270,054 discloses N-2-adamant-1-yl- and N-2-homoadamant-1-yl-oxy-ethyl-thioethyl- and aminoethyl-guanidine derivatives bearing at most two lower alkyl groups on the N'- and/or N''-nitrogen atom as sympathicolytic and anti-viral agents;

U.S. Pat. No. 3,301,755 discloses N-ethylenically unsubstituted-alkyl-guanidines and the corresponding N'- and/or N''-lower alkyl compounds as hypoglycemic and antihypertensive agents;

U.S. Pat. No. 3,409,669 discloses N-cyclohexylamino-(3,3-dialkyl-substituted-propyl)-guanidines and the corresponding N'-alkyl- and/or N''-alkyl-substituted compounds as hypotensive agents;

U.S. Pat. No. 3,547,951 discloses 1,3-dioxolan-4-yl-alkyl-substituted guanidines which have antihypertensive activity and discloses lower alkyl, including n-butyl, as a possible substituent on the other amino group;

U.S. Pat. No. 3,639,477 discloses propoxylguanidine compounds as having anorectic properties;

U.S. Pat. Nos. 3,681,459; 3,769,427; 3,803,324; 3,908,013; 3,976,787; and 4,014,934 disclose aromatic substituted guanidine derivatives wherein the phenyl ring can contain hydroxy and/or halogen substituents for use in vasoconstrictive therapy;

U.S. Pat. No. 3,804,898 discloses N-benzylcyclobutenyl and N-benzylcyclo-butenyl-alkyl-guanidines and the corresponding N-alkyl and/or N''-alkyl-substituted compounds as hypotensive agents;

U.S. Pat. No. 3,968,243 discloses N-aralkyl substituted guanidines and the corresponding N'-alkyl n''alkyl and N',N'-aralkyl compounds as being useful in the treatment of cardiac arrhythmias;

U.S. Pat. No. 3,795,533 discloses o-halo-benzylidene-amino-guanidines and their use as anti-depressants for overcoming psychic depression;

U.S. Pat. No. 4,007,181 discloses various N,N'-disubstituted guanidines substituted on the imine nitrogen atom by adamantyl as possessing antiarrhythmic and diuretic activities;

U.S. Pat. No. 4,051,256 discloses N-phenyl- and N-pyridyl-N'-cycloalkyl-guanidines as antiviral agents;

U.S. Pat. Nos. 4,052,455 and 4,130,663 disclose styrylamidines, as analgesics agents or for the prevention of blood platelet aggregation;

U.S. Pat. No. 4,109,014 discloses N-hydroxysubstituted guanidines and the corresponding N-methyl disubstituted guanidines as vasoconstrictor agents;

U.S. Pat. No. 4,169,154 discloses the use of guanidines in the treatment of depression;

U.S. Pat. No. 4,393,007 discloses N-substituted and unsubstituted, N-substituted methyl-N'-unsubstituted, monosubstituted and disubstituted-N''-unsubstituted and substituted guanidines as ganglionic blocking agents; and U.S. Pat. No. 4,471,137 discloses N,N,N'N''-tetraalkyl guanidines as being sterically hindered bases useful in chemical synthesis.

U.S. Pat. No. 4,709,094 discloses 1,3-disubstituted-guanidines, e.g., 1-3-dibutyl-guanidine and 1,3 di-o-tolyl-quinidine, as sigma brain receptor ligands.

For examples of other substituted guanidines, see, e.g., U.S. Pat. Nos. 1,422,506; 1,642,180; 1,756,315; 3,159,676; 3,228,975; 3,248,426; 3,283,003; 3,320,229; 3,479,437; 3,547,951; 3,639,477; 3,784,643; 3,949,089; 3,975,533; 4,060,640 and 4,161,541.

Geluk, H. W., et al., *J. Med. Chem.*, 12,712 (1969) describe the synthesis of a variety of adamantyl disubstituted guanidines as possible antiviral agents, including N,N'-di-(adamantan-1-yl)-guanidine hydrochloride, N-(adamantan-1-yl)-N'-cyclohexyl-guanidine hydrochloride and N-(adamantan-1-yl)-N'-benzyl-guanidine hydrochloride.

U.S. Pat. No. 4,709,094 (1987), discloses N,N'-disubstituted guanidine derivatives which exhibit high binding activity with respect to the sigma receptor having the Formula (I):

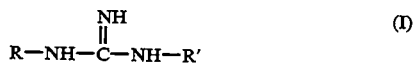

wherein R and R' are an alkyl group of at least 4 carbon atoms, a cycloalkyl group of 3-12 carbon atoms, or carbocyclic or aryl, of at least 6 carbon atoms.

Two of the novel N,N'-disubstituted guanidines disclosed therein are also claimed therein viz., 1,3-di-(4-halo-2-methylphenyl)-guanidine and 1,3-di-(4-$^3$H]-(2-methylphenyl)-guanidine.

Also claimed therein is a method of determining the relationship of abnormal psychotic-like behavior in a mammal displaying such behavior to sigma receptor system dysfunction, which comprises administering to the mammal displaying such behavior a water-soluble N,N'-disubstituted-guanidine which displaces in vitro N,N'-di-(4-[$^3$H]-2-methylphenyl)-guanidine bound to mammalian brain membrane, in an amount effective to alter the sigma brain receptor-modulated mental activity of the mammal; a method of treating a human being suffering from a psychotic mental illness associated with hallucinations, which comprises administering thereto a water-soluble N,N'-disubstituted guanidine which is an antagonist to the sigma receptor binding activity of a hallucinogenic benzomorphan, in an amount effective to ameliorate the hallucinations.

In U.S. Pat. No. 4,709,094 is further disclosed a method of determining the sigma brain receptor binding activity of an organic compound which comprises the steps of a) contacting in an aqueous medium a known amount of isolated mammalian brain membrane which has sigma receptor-like binding activity, with a mixture of (i) a tritium labeled N,N'-disubstituted guanidine which selectively binds sigma brain receptors, in a known amount capable of being bound to the sigma receptors of that brain membrane; and (ii) varying known amounts of a water soluble organic compound to be assayed for sigma receptor binding activity; b) separating the brain membrane from the tritium labeled compound which is not bound to the brain membrane in step a); and c) determining, from the molar relationship of the proportion of bound tritium-labeled compound which is separated in step b) to the molar amount of the organic compound employed in step a), the sigma receptor binding activity of that organic compound.

Certain benzomorphan opiates, such as N-allyl-normetazocine (SKF 10,047) and cyclazocine, in addition to analgesia, cause hallucinations, depersonalization, drunkenness and other psychotomimetic effects in man. In monkeys, dogs and rodents the psychotomimetic opiates cause behavioral and autonomic effects that are unlike those observed with administration of classical opiates such as morphine or the opioid peptides. Specific sigma "opioid" receptors in the brain are believed to mediate such atypical effects. Martin et al., *J. Pharmacol. Exp. Ther.* 197:517–532 (1976). It is believed that the sigma receptors also mediate some of the psychotomimetic effects of phencyclidine [PCP, angel dust], or alternatively, that psychotomimetic opiates act at specific PCP receptors. Zukin, R. S., et al., *Mol. Pharmacol.* 20:246–254 (1981); Shannon, H. E., *J. Pharmacol. Exp Ther.* 225:144–152 (1983); White, J. M., et al., *Psychopharmacology* 80:1–9 (1983); and Zukin et al., *J. Neurochem.* 46:1032#1041 (1986). PCP is a drug of abuse that causes a behavioral syndrome in man similar to that which is observed in schizophrenic psychosis. Aniline, O., et al., *CRC Critical Rev, Toxicol.* 10:145–177 (1982). Because of the potent psychotomimetic effects of sigma opiates and PCP, it is believed that sigma (and/or PCP) receptors play a role in mental illness, particularly schizophrenia.

A systematic investigation of the role of sigma receptors in normal and abnormal brain function has been hindered by a lack of specific sigma receptor binding assays and bioassays. Development of such specific assays requires well-characterized, highly selective and potent sigma receptor ligands. Recent studies have shown that brain membrane receptors can be labeled in vitro with (+)[$^3$H]SKF 10,047, Su, T. P., *J. Pharmacol. Exp. Ther.* 223:284–290 (1982); (+)[$^3$H]SKF 10,047, Tam, S. W., et al., *Proc. Natl. Acad. Sci. U.S.A.* 81:5618–5621 (1984); Martin et al., *J. Pharmacol. Exp. Ther.* 231:539–544 (1984); and Mickelson, M. M., et al., *Res. Commun. Chem. Pathol. Pharmacol.* 47:255–263 (1985), although not selectively, Gundlach et al., *Eur. J. Pharmacol.* 113:465–466 (1985); and Largent, B. L., et al., *J. Pharmacol. Exp. Ther.* 238:739–748 (1986), and with (+)[$^3$H]3-(3-hydroxyphenyl)-N-(1-propyl)-piperidine ((+)[³H]3-PPP), Largent et al., *Proc. Natl. Acad. Sci. U.S.A.* 81:4983–4987 (1984), which is apparently more selective for sigma receptors than the others.

After the initial in vitro studies by Martin et al., (1976) supra, Keats and Telford (Keats, A. S., et al., "Analgesics: Clinical Aspects." In *Molecular Modification in Drug Design*, R. F. Gould (ed.), Advances in Chemistry Series #45 Amer. Chem. Soc., Wash. D.C. (1964)), and Haertzen (Haertzen, C. A. Cyclazocine and Nalorphine on the Addiction Research Center Inventory (ARCI), *Psychopharmacologia* (Berl.) 18:366–377 (1970)), numerous investigators set out to biochemically characterize the different opiate receptors (mu receptors, kappa receptors and sigma receptors) in vitro.

The first evidence for the existence of a separate sigma receptor in test tube experiments was provided by Su (1982) supra in a paper describing an etorphine-inaccessible binding site in guinea pig brain membranes which was apparently selectively labeled by tritium-labeled SKF-10,047. To overcome the fact that SKF10,047 could label multiple opioid receptors in the brain, Su performed his receptor binding assay using tritium labeled SKF-10,047 in the presence of excess unlabeled etorphine. Etorphine is a very strong opiate agonist drug which is known to bind to delta receptors, mu receptors and kappa receptors with almost equal potency. Su used etorphine to saturate all mu, kappa and delta receptors in a brain membrane preparation and then added tritium labeled SKF-10,047. This enabled him to detect a sigma binding site that was apparently different from mu, kappa and delta receptors. A major breakthrough in identifying the sigma receptor as a separate entity occurred when Tam et al. (1984), supra, demonstrated that the previous problems in selectively labeling the sigma receptor were caused by the fact that in all previous experiments a racemic SKF-10,047 preparation was used. Tam showed that using a tritium labeled (+)-SKF-10,047 isomer one could selectively label a sigma receptor that was different from the mu, delta and kappa opioid receptors. On the other hand, Tam showed that (−)-SKF-10,047 apparently labeled the mu and kappa receptors but not the sigma receptors. Tam, S. W., *Eur. J. Pharm.* 109:33–41 (1985). This finding has now been confirmed. (Martin et al., 1984, supra). Moreover, there is evidence from behavioral experiments, Khazan et al., *Neuropharm.* 23:983–987 (1984); Brady et al., *Science* 215:178–180 (1981), that it is the (+)-SKF-10,047 isomer that is solely responsible for the psychotomimetic effects of SKF-10,047.

One of the most important findings of the biochemical characterization of the sigma receptor has been that this receptor binds all synthetic opiate drugs that are known to have hallucinogenic and psychotomimetic effects. Opiates that do not have psychotomimetic effects in vivo do not bind to this receptor. Most importantly, it has been shown that besides hallucinogenic opiate drugs, the sigma receptor also binds many antipsychotic drugs that are used clinically to treat hallucinations in schizophrenic patients. (Tam and Cook, 1984). The initial observations with regard to antipsychotic drug binding to the sigma receptor (Su, 1982) were subsequently extensively confirmed and extended by Tam et al. (1984), supra, also showed that when one used radioactively labeled haloperidol, one of the most potent antipsychotic drugs that is used clinically, about half of the binding sites in brain membrane preparations are actually sigma receptors whereas the other half of the binding sites are apparently dopamine receptors. It has long been known that most antipsychotic drugs are also dopamine receptor antagonists. Previously the beneficial actions of antipsychotic drugs in psychotic patients have been attributed to the dopamine receptor-blocking effect of these drugs. It is clear from the work by Tam, however, that numerous clinically used antipsychotic drugs also bind to the sigma site. All antipsychotic drugs that bind to the sigma receptor may in part cause the beneficial effect of alleviating hallucinations through the sigma receptor. Taken together all these observations suggest the sigma receptor as a prime candidate to be involved in the pathogenesis of mental illness, particularly schizophrenia in which hallucinations are a major clinical symptom.

Deutsch, S. I., et al. (*Clinical Neuropharmacoloy*, Vol. 11, No. 2, pp. 105–119 (1988)) provided a review of the literature which implicates the sigma receptor site in psychosis and anti-drug efficacy. According to Deutsch et al., certain benzomorphans which possess analgesic potency in humans are also associated with a high incidence of psychotomimetic effects. It has now been concluded that the analgesic action is associated with the levorotatory isomers of racemic mixtures of the benzomorphans, while the psychotomimetic effects are attributable to the dextrorotatory isomers in the racemic mixtures. See Haertzen, C. A., *Psychopharmacologia* 18:366–77 (1970), and Manallack, D. T., et al., *Pharmacol. Sci.* 7:448–51 (1986). Coupled with the fact that many of the in vivo effects of these dextrorotatory enantiomers and the binding of dextrorotatory tritiated SKF-10,047 are not antagonized by naloxone or naltrexone, these data strongly support the concept that the psychotomimetic effects of the dextrorotatory enantiomers are associated with the sigma receptor binding site.

Further, Su, T. P., et al. (*Life Sci.* 38:2199–210 (1986)), and Contreras, P. C., et al. (*Synapse* 1:57–61 (1987)), have established the existence of endogenous ligands for the sigma receptor, suggesting that the dysregulation of the synthesis, release, or degradation of these natural ligands may be a naturally occurring mechanism of psychosis. Accordingly, sigma receptor antagonism provides the potential for an effective antipsychotic therapeutic treatment. See Ferris, R. M., et al., *Life Sci.* 38:2329–37 (1986), and Su, T. P., *Neurosci. Let.* 71:224–8 (1986).

As further evidence of the role of the sigma receptor in psychosis, the substituted carbazole cis-9-[3-(3,5-dimethyl-1-piperazinyl)propyl]carbazole dihydrochloride (rimcazole) was identified as a potential antipsychotic agent based on its ability to antagonize apomorphine-induced mesolimbic behaviors selectively without altering the intensity of stereotypic behaviors. Further, the compound does not accelerate the rate of dopamine synthesis and does not affect dopamine-stimulated production of cAMP in homogenates of rat striatum and olfactory tubercle, thus establishing that rimcazole does not exert its action at the level of postsynaptic dopamine receptors in the mesolimbic area.

Rimcazole is able to competitively inhibit the specific binding of dextrorotatory tritiated SKF-10,047, the prototype sigma receptor agonist, suggesting that rimcazole acts at the sigma receptor site. Rimcazole, therefore, shows potential antipsychotic activity in humans, without extrapyramidal effects, pharmacological behavior which is consistent with its role as a competitive antagonist of the sigma-receptor.

Another compound, BMY 4802, has demonstrated many properties in preclinical behavioral tests which suggest its efficacy as a potential antipsychotic agent which is devoid of extrapyramidal side effects. The compound (1) did not cause catalepsy in rats; (2) does not inhibit the binding of [$^3$H]spiperone to the $D_2$ class of striatal dopamine receptors in rats; (3) did not increase the maximal density of the [$^3$H]spiperone-labeled $D_2$ site in striatum even following chronic administration (20 days) to rats; (4) does not appear to interact with the $D_1$ subclass of dopamine receptors; and (5) does not inhibit dopamine-stimulated cAMP production or the binding of [$^3$H]SCH 23390 in vitro. These data suggest that BMY 14802 has a low potential for production of tardive dyskinesia and further suggests that the antipsychotic effects would be mediated by a non-dopaminergic site. Further, BMY 14802 binds with relatively high affinity to the sigma receptor, with the binding being stereoselective (the dextrorotatory enantiomer being 10 times more potent at inhibiting binding than the levorotatory enantiomer). BMY 14802 does not bind to the adrenergic, muscarinic, cholinergic, or histaminergic sites, suggesting that the compound would not be associated with unpleasant sedative and autonomic side effects.

Accordingly, compounds which bind selectively to the sigma receptor site and which antagonize this site may be expected to be useful antipsychotic drugs which are devoid of extrapyramidal effects.

The antipsychotic and anti-schizophrenia drugs that are currently in use have very strong side effects that are mainly due to their action on dopamine receptors. The side effects often involve irreversible damage to the extrapyramidal nervous system which controls movement functions of the brain. Patients under long term anti-schizophrenic drug treatment often develop a syndrome that involves permanent damage of their ability to control coordinated movement.

The foregoing studies have shown that the sigma binding site has the characteristics of 1) stereo-selectivity towards dextrorotatory benzomorphan opiates and insensitivity for naloxone; 2) high affinity for haloperidol and moderate to high affinity for phenothiazine antipsychotic drugs which are also known to be potent dopamine receptor blockers; and 3) insensitivity for dopamine and apomorphine. This intriguing drug selectivity profile calls for a thorough analysis of the role of sigma receptors in normal and abnormal brain function. In order to do so, it is essential that a spectrum of highly selective and potent sigma receptor active compounds be available. This invention provides such compounds and methods for identifying other drugs having such activity.

SUMMARY OF THE INVENTION

The invention relates to novel N,N'-disubstituted guanidines which bind to sigma receptor sites, especially those which do so selectively.

The invention also relates to a novel class of N,N'-disubstituted guanidines which are radioactively tagged and which are useful for assaying in vitro the sigma receptor binding activity of organic compounds.

The invention also relates to pharmacological compositions comprising certain of the aforesaid N,N'-disubstituted guanidines having sigma receptor binding activity.

The invention also relates to a method for determining the sigma receptor binding activity of organic compounds.

The invention also relates to an in vitro screening method for assaying compounds having sigma receptor activity and utility as antipsychotic and antidepressant drugs.

The invention also relates to a method for treating abnormal psychotic-like behavior in mammals, in particular, humans, and pharmacological compositions comprising N,N'-disubstituted guanidine compounds which are efficacious in the treatment of such abnormal psychotic-like behavior.

The invention also relates to a method of determining the relationship of abnormal psychotic-like behavior in a mammal displaying such behavior to sigma receptor system dysfunction.

The invention also relates to N,N-disubstituted guanidine pharmaceutical compositions comprising said N,N'-disubstituted guanidine compounds, and methods for using same to treat hypertension.

The substituted guanidines of the invention have the Formula (I):

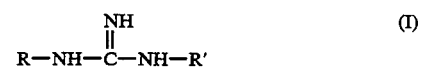

wherein R and R' are an alkyl group of at least 4 carbon atoms, a cycloalkyl group of at least 3 carbon atoms, a carbocyclic aryl group of at least 6 carbon atoms, alkaryl or aralkyl of at least 6 carbon atoms and containing 1–3 separate or fused rings, or a heterocyclic ring, and wherein each of R and R' may be substituted in 1–3 positions, or wherein R and R' together with the guanidine group to which they are attached form a saturated or unsaturated cyclic ring containing at least 2 carbon atoms exclusive of the guanidine carbon atom, and wherein said cyclic ring may be substituted with one or more alkyl groups of 1–6 carbon atoms, carbocyclic aryl groups of at least 6 carbon atoms, cycloalkyl groups of 3–12 carbon atoms, or 1–2 fused aromatic rings, and further wherein said N,N'-disubstituted guanidine exhibits a high affinity for the sigma receptor. Preferably, such N,N'-disubstituted guanidines also exhibit antipsychotic and/or antihypertensive activity in an animal, for example, in an animal model.

In particular, the invention relates to N,N'-disubstituted guanidines of the Formula (I), above, wherein R and R' each are adamantyl, cyclohexyl or a monocyclic carbocyclic aryl of at least 6 carbon atoms.

The invention also relates to substituted guanidines having the Formula (II):

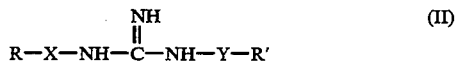

wherein

X and Y are independently a branched or straight chain $C_1$–$C_{12}$ alkylene or a branched or straight chain $C_2$–$C_{12}$ unsaturated alkylene or wherein one of X and Y is a single bond;

R and R' are independently hydrogen, a cycloalkyl group of at least 3 carbon atoms, a carbocyclic aryl group of at least 6 carbon atoms, aralkyl of at least 6 carbon atoms and containing 1–3 separate or fused rings, or a heterocyclic ring, and wherein each of R and R' may be substituted in 1-3 positions, or wherein R and R' together with the guanidine group to which they are attached form a saturated or unsaturated cyclic ring containing at least 4 carbon atoms exclusive of the guanidine carbon atom, and wherein said cyclic ring may be substituted with one or more alkyl groups of 1-6 carbon atoms, carbocyclic aryl groups of at least 6 carbon atoms, cycloalkyl groups of 3-12 carbon atoms, or 1-2 fused aromatic rings. Preferably, said N,N'-disubstituted guanidine exhibits a high affinity for the sigma receptor.

The invention also relates to compounds having the formula:

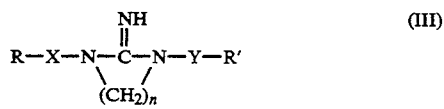

where in n is 2, 3, 4 or 5;

X and Y are independently a single bond, a branched or straight chain $C_1$-$C_{12}$ alkylene or a branched or straight chain $C_2$-$C_{12}$ alkylene; R and R' are independently hydrogen, a cycloalkyl group of at least 3 carbon atoms, a carbocyclic aryl group of at least 6 carbon atoms, aralkyl of at least 6 carbon atoms and containing 1-3 separate or fused rings, a heterocyclic ring, and wherein each of R and R' may be substituted in 1-3 positions, or wherein R and R' together with the guanidine group to which they are attached form a saturated or unsaturated cyclic ring containing at least 4 carbon atoms exclusive of the guanidine carbon atom, and wherein said cyclic ring may be substituted with one or more alkyl groups of 1-6 carbon atoms, carbocyclic aryl groups of at least 6 carbon atoms, cycloalkyl groups of 3-12 carbon atoms, or 1-2 fused aromatic rings; wherein said compound exhibits a high affinity for the sigma receptor.

The invention also relates to tritiated derivatives of the above-listed N,N'-disubstituted guanidines wherein at least one of the ring carbon atoms of R and R' bears at least one tritium atom The invention also relates to pharmaceutical compositions, in unit dosage form and adapted for systemic administration to a human being, which comprises, per unit dosage, an amount effective to alter the sigma brain receptor-modulated activity of a human being displaying psychotic behavior or suffering from chronic depression, of an N,N'-disubstituted guanidine in its water-soluble protonated form which displaces in vitro N,N'-di-(4-[$^3$H]-2-methylphenyl)-guanidine bound to isolated mammalian brain membrane.

The invention also relates to a method of determining the sigma brain receptor binding activity of an organic compound which comprises the steps of:

a) contacting in an aqueous medium a known amount of isolated mammalian brain membrane which has sigma receptor-type binding activity, with a mixture of (i) a tritium-labeled N,N'-disubstituted guanidine which selectively binds sigma brain receptors, in a known amount capable of being bound to the sigma receptors of that brain membrane; and
(ii) varying known amounts of a water soluble organic compound to be assayed for sigma receptor binding activity;

b) separating the brain membrane from the tritium labeled compound which is not bound to the brain membrane in step a);

c) determining, from the molar relationship of the proportion of bound tritium labeled compound which is separated in step b) to the molar amount of the organic compound employed in step a), the sigma receptor binding activity of that organic compound.

The invention also relates to a method of determining the relationship of abnormal psychotic-like behavior in a mammal displaying such behavior to sigma receptor dysfunction, which comprises administering thereto a sigma brain receptor-modulating amount of a water-soluble N,N'-disubstituted guanidine which displaces in vitro N,N'-di-(4-[$^3$H]-2-methylphenyl)-guanidine bound to mammalian brain membrane, effective to alter the sigma brain receptor-modulated mental activity of that mammal.

The invention also relates to a method of treating a human being suffering from chronic depression or a psychotic mental illness associated with hallucinations, e.g., schizophrenia, which comprises administering thereto a water soluble N,N'-disubstituted-guanidine which is an antagonist to the sigma receptor binding activity of a hallucinogenic benzomorphan, and/or which displaces in vitro N,N'-di-(4-[$^3$H]-2-methylphenyl)-guanidine bound to mammalian brain membrane, preferably a compound of Formulae (I) or (II), in an amount effective to ameliorate the depression or hallucinations, respectively.

The invention also relates to the use of the N,N'-disubstituted guanidines for the treatment of hypertension.

By the present invention, there is provided a means for identifying compounds which bind competitively and selectively to the sigma receptor site. Accordingly, the invention provides compounds, pharmaceutical compositions, and the use of same for treatment of psychoses. Selective sigma receptor binding is of particular value in reducing or eliminating undesirable extrapyramidal side effects associated with present antipsychotic medications. Further, these compounds are useful for the treatment of hypertension.

DESCRIPTION OF THE PREFERRED EMBODIMENTS

We have discovered that the disubstituted guanidines of this invention have-sigma receptor binding activity, as evidenced by their ability to displace from guinea pig membrane binding sites [$^3$H]-1,3-di-ortho-tolyl-guanidine (N,N'-di-(4-[$^3$H]-2-methylphenyl)-guanidine ([$^3$H]-DTG]) which has the Formula (III):

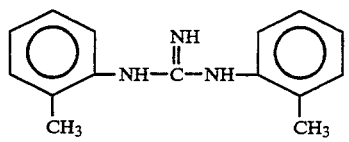

binds reversibly, saturably, selectively and with high affinity to sigma receptor binding sites in guinea pig brain membrane homogenates and slide-mounted rat and guinea pig brain sections. We have established that (+)-[$^3$H]3-PPP binds to the same sites. Availability of the selective sigma ligands of this invention facilitates characterization of sigma receptors in vivo and in vitro.

The preferred N,N'-disubstituted guanidines of this invention are those of the Formula (I):

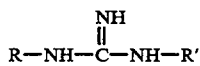

wherein R and R' each are an alkyl group of at least 3 carbon atoms or carbocyclic aryl groups of at least 6 carbon atoms, e.g., R and R', which can be the same or different, are alkyl of 4 or more carbon atoms, e.g., a 4 to 12, preferably a straight chain alkyl and more preferably a 4 to 8 carbon atom alkyl group, for example, butyl, isobutyl, tert-butyl, amyl, hexyl, octyl, nonyl and decyl; cycloalkyl of 3 to 12 carbon atoms, e. g., cyclopropyl, cyclobutyl, cyclopentyl, cyclohexyl, cycloheptyl, 1,4-methylene-cyclohexanyl, adamantyl, cyclopentylmethyl, cyclohexylmethyl, 1- or 2-cyclohexylethyl and 1-, 2- or 3-cyclohexylpropyl; carbocyclic aryl, alkaryl or aralkyl, e.g., of up to 18 carbon atoms and containing 1-3 separate or fused aromatic rings, e.g., phenyl, benzyl, 1- and 2-phenylethyl, 1-, 2-, or 3-phenylpropyl; o-, m- or p-tolyl, m,m'-dimethylphenyl, o-, m- or p-ethylphenyl, m,m'diethylphenyl, m-methyl-m'-ethylphenyl and o-propylphenyl, naphthyl, 2-naphthyl, biphenyl; and heterocyclic rings, e.g., 2- and 4-pyridyl, pyrrolyl especially 2- and 3-N-methylpyrrolyl, 2- and 3-furanyl, 2- and 3-thiophenyl, 2- and 3-benzofuranyl, 2-benzoxazolyl, pyrazinyl, pyrimidyl, 2-, 4- and 5- thiazolyl, 2-, 4- and 5-oxazolyl, 2-, 4- and 5-imidazolyl, 2- and 3-indolyl, and 2- and 4-benzothiazolyl.

Additionally, 1, 2, 3 or more substituents which do not adversely affect the activity of the N,N'-disubstituted guanidine moiety may be present on one or both of the R and R' hydrocarbon groups thereof, e.g., alkyl of 1-8 carbon atoms, e.g., methyl, ethyl; hydroxyalkyl of 1-8 carbon atoms; halo, e.g., chloro, bromo, iodo, fluoro; hydroxy; nitro; azido, cyano; isocyanato; amino; lower-alkylamino; di-lower-alkylamino; trifluoromethyl; alkoxy of 1-8 carbon atoms, e.g., methoxy, ethoxy and propoxy; acyloxy, e.g., alkanoyloxy of 1-8 carbon atoms, e.g., acetoxy and benzoyl; amido, e.g., acetamido, N-ethylacetamido; carbamido, e.g., carbamyl, N-methylcarbamyl, N,N'-dimethyl-carbamyl; etc.

Especially preferred are compounds of Formula I wherein R and R' each are phenyl groups, which need not necessarily be identical, substituted with one or more of the foregoing substituents, for example, in the o-, m- or p- position or the 2,2-, 2,4- or 3,5-position, when the phenyl group is disubstituted or R is as herein defined and R' is adamantyl. Specific examples are those wherein R and R' both are phenyl or o-tolyl; R is o-tolyl and R' is p-bromo-o-tolyl, p-CF$_3$-o-tolyl, p-iodo-o-tolyl, o-iodo-phenyl, p-azido-o-tolyl, cyclohexyl or adamantyl; and R is phenyl and R' is p-bromo-o-tolyl, p-iodo-o-tolyl, m-nitro-phenyl or o-iodo-phenyl.

The highly active disubstituted guanidines of this invention, e.g., DTG, have substantially the same stereoconfiguration as (+)3-PPP with phenyl axial and with SKF 10,047 with the piperidine ring in a skew-boat form and N-allyl axial. This similarity in spacial configuration, i.e., as demonstrated by computer modeling, of compounds having sigma receptor binding activity provides a screening technique for predicting the probable level of sigma receptor binding activity of other N,N'-disubstituted guanidines. Computer assisted molecular modifying can be used to determine the molecular similarity of the various species in three dimensions.

Examples of those compounds which have been isolated and/or prepared and found to possess the aforesaid in vitro [$^3$H]DTG displacement activity are N,N'-dibutylguanidine, N,N'-diphenylguanidine, N,N'-di-o-tolylguanidine, N,N'-di-(2-methyl-4-bromo-phenyl)-guanidine, N,N'-di-(2-methyl-4-iodophenyl)guanidine, N-(2-methyl-azidophenyl)-N'-(2-methylphenyl)guanidine, N,N'-diadamantylguanidine, N-adamantyl-N'-(2-methylphenyl)guanidine, N-(2-iodophenyl)-N'-(2-methylphenyl)guanidine, N-(2-methyl-4-nitrophenyl)-N'-(2-methylphenyl)guanidine, N,N'-di-(2,6-dimethylphenyl)guanidine, N-(2,6-dimethylphenyl)-N'-(2-methylphenyl)-N'-(2-methylphenyl)guanidine, N-(adamantyl)-N'-(cyclohexyl)guanidine, N,N'-di(cyclohexyl)guanidine, N-(2-iodophenyl)-N'-(adamantyl)-guanidine, N-(2-methylphenyl)-N'-cyclohexyl-guanidine, N-adamantly-N'-phenylguanidine, N-(o-tolyl)-N'-(o-iodophenyl)guanidine, N,N'-di-(p-bromo-o-methylphenyl)guanidine, N,N'-di-(m-n-propylphenyl)guanidine, N-(o-tolyl)-N'-(p-nitro-o-tolyl)guanidine, N,N'-di-(1-tetralinyl)guandidine, N-(o-tolyl)-N'-(o-xylyl)guanidine, N,N'-di-(o-xylyl)guanidine, N,N'-di-(cyclohexyl)-guanidine, N-(3,5-dimethyl-1-adamantanyl)-N'-(o-tolyl)guanidine, N-(3,5-dimethyl-1-adamantanyl)-N'-o-iodophenyl)guanidine, N-(1-adamantyl)-N'-(o-nitrophenyl)guanidine, N,N'-di-((±)-endo-2-norbornyl)-guanidine, N-(exo-2-isobornyl)-N'-(o-iodophenyl)-guanidine, N,N'-di-(exo-2-norbornyl)guanidine, N-(exo-2-isobornyl)-N'-(o-tolyl)guanidine, N-(o-iodophenyl)-N'-(t-butyl)guanidine, N,N'-dibenzylguanidine, N-(adamant-1-yl)-N'-(o-isopropylphenyl)guanidine, N-(adamant-1-yl)-N'-(p-bromo-o-tolyl)guanidine, N-(cyclohexyl)-N'-(p-bromo-o-tolyl)guanidine, and N-(adamant- 2-yl)-N'-(p-iodophenyl)guanidine.

Among the compounds tested to date, some of those having the highest sigma receptor binding activity are those of Formula I wherein one of R and R' is adamantyl and the other is also adamantyl or o-substituted phenyl. Therefore, the preferred compounds of this invention include those wherein R and R$^1$ have those values, i.e., wherein the other of R and R$^1$ is, e.g., o-lower alkyl phenyl, wherein alkyl is of 1-4 carbon atoms, e.g., CH$_3$, C$_2$H$_5$, i-C$_3$H$_7$, o-halophenyl wherein halo is Cl, Br, I or F, o-nitro-o-amino, o-carbo-lower alkoxy, e.g., COOCH$_3$, o-amino, e.g., —CONH$_2$, o-sulfato, o-carboxy, o-acyl, e.g., acetyl, o-CF$_3$, o-sulfamido and o-lower-alkoxy, e.g., o-methoxy, phenyl or another phenyl group ortho substituted by any other substituent of a molecular weight less than 150.

Included in the substituted guanidines useful in the practice of this invention are those which have the Formula (I):

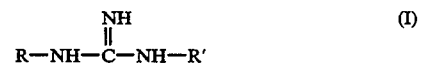

wherein R and R' are an alkyl group of at least 3 carbon atoms, a cycloalkyl group of at least 3 carbon atoms, a carbocyclic aryl group of at least 6 carbon atoms, alkaryl or aralkyl of at least 6 carbon atoms and containing 1-3 separate or fused rings, or a heterocyclic ring, and wherein each of R and R' may be substituted in 1-3 positions, or wherein R and R' together with the guanidine group to which they are attached form a cyclic ring containing at least 2 carbon atoms exclusive of the guanidine carbon atom, and wherein said cyclic ring may be substituted with one or more alkyl groups of 1–6 carbon atoms, carbocyclic aryl groups of at least 6 carbon atoms, cycloalkyl groups of 3–12 carbon atoms, or 1–2 fused aromatic rings, and further wherein said N,N'-disubstituted guanidine exhibits a high affinity for the sigma receptor.

Preferred N,N'-disubstituted guanidines which are useful in the practice of this invention are those wherein R and R', which need not be identical, are an alkyl group of at least 3 carbon atoms or carbocyclic aryl groups of at least 6 carbon atoms, e.g., R and R', which can be the same or different, are alkyl of 4 or more carbon atoms, e.g., a 4 to 12 carbon atom, preferably a straight chain alkyl group and more preferably a 4 to 8 carbon atom alkyl group, for example, butyl, isobutyl, tert-butyl, amyl, hexyl, octyl, nonyl and decyl; cycloalkyl of 3 to 12 carbon atoms, e.g., cyclopropyl, cyclopentyl, cyclohexyl, cycloheptyl, 1,4-methylenecyclohexane, adamantyl, cyclopentylmethyl, cyclohexylmethyl, 1- or 2-cyclohexylethyl and 1-, 2- or 3-cyclohexylpropyl; carbocyclic aryl, alkaryl or aralkyl, e.g., of up to 18 carbon atoms and containing 1–3 separate or fused aromatic rings, e.g., phenyl, benzyl, 1- and 2-phenylethyl, 1-, 2-, or 3-phenylpropyl; o-, m-, or p-tolyl, m,m'-dimethylphenyl, o-, m-, or p-ethylphenyl, m,m'-diethylphenyl, m-methyl-m'-ethylphenyl and o-propylphenyl, naphthyl, 2-naphthyl, and biphenyl, and heterocyclic aromatic rings including pyridyl, pyrazinyl, pyrimidyl, furyl pyrolyl, thienyl, thiazolyl, oxazolyl, imidazolyl, indolyl, and benzothiazolyl.

Additionally, 1, 2, 3 or more substituents which are chemically and physiologically substantially inert compared to the guanidine group may be present on the R and R' hydrocarbon groups, e.g., alkyl of 1–8 carbon atoms, e.g., methyl, ethyl; hydroxyalkyl of 1–8 carbon atoms; hydroxy; halo, e.g., chloro, bromo, iodo, fluoro; nitro; azido; cyano; isocyano; amino; lower-alkylamino; di-lower-alkylamino; trifluoromethyl; alkoxy of 1–8 carbon atoms, e.g., methoxy, ethoxy and propoxy; acyloxy, e.g., alkanoyloxy of 1–8 carbon atoms, e.g., acetoxy and benzoxy; amido, e.g., acetamido, N-ethyl acetamido; carbamido, e.g., carbamyl, N-methylcarbamyl, N,N'-dimethylcarbamyl; etc.

A preferred class of compounds of Formula I are those wherein R and R', which need not be necessarily identical, are phenyl or substituted phenyl groups, cyclohexyl, norbornyl, adamant-1-yl and adamant-2-yl groups. Substituted phenyl groups may have one or more of the foregoing substituents, for example, in the o-, m- or p-position or the o-, p- or m, m'-position, when the phenyl group is disubstituted, or R is as herein defined and R' is adamantyl.

Especially preferred N,N'-disubstituted guanidine compounds which have high binding to the sigma receptor include N-(2-iodophenyl)-N'-(adamant-1yl)-guanidine (AdIpG, IC$_{50}$=6.2 nM); N-(o-tolyl)-N'-(adamant-1-yl)guanidine (AdTG, IC$_{50}$=7.6 nM); N,N'-di-(adamant-1yl)guanidine (DAG, IC$_{50}$=16.5 nM); N-cyclohexyl-N'-(2-methylphenyl)guanidine (IC$_{50}$=13 nM); N-(adamant-1-yl)-N'-cyclohexylguanidine (IC$_{50}$=12.5 nM); N-(adamant-2-yl)-N'-(2-iodophenyl)-guanidine (IC$_{50}$=3.5 nM); N-(adamant-2-yl)-N'-(2-methylphenyl)guanidine (IC$_{50}$=7.0 nM); N-(exo-2-norbornyl)-N'-(2-methylphenyl)guanidine (IC$_{50}$=7.0 nM); N-(($\pm$)-endo-2-norbornyl)-N'-(2-methylphenyl)guanidine (IC$_{50}$=6.0 nM); N-(exo-2-norbornyl)-N'-(2-iodophenyl)guanidine (IC$_{50}$=4.0 nM); N-(($\pm$)-endo-2-norbornyl)-N'-(2-iodophenyl)guanidine (IC$_{50}$=5.0 nM); N,N'-di-(o-tolyl)guanidine (IC$_{50}$=32 nM); N-(o-tolyl)-N'-(o-iodophenyl)guanidine (IC$_{50}$=21 nM); N,N'-di-(p-bromo-o-methylphenyl)guanidine (IC$_{50}$=37 nM); N,N'-di-(m-n-propylphenyl)guanidine (IC$_{50}$=36 nM); N-(o-tolyl)-N'-(p-nitro-o-tolyl)guanidine (IC$_{50}$=37 nM); N,N'-di-(1-tetralinyl)guanidine (IC$_{50}$=58 nM); N-(o-tolyl)-N'-(o-xylyl)guanidine (IC$_{50}$=70 nM); N,N'-di-(o-xylyl)guanidine (IC$_{50}$=90 nM); N,N'-di-(cyclohexyl)guanidine (IC$_{50}$=71 nM); N-(3,5-dimethyladamantan-1-yl)-N'-(o-tolyl)guanidine (IC$_{50}$=15 nM); N-(3,5-dimethyl-1-adamantanyl)-N'-(o-iodophenyl)guanidine (IC$_{50}$=16 nM); N-(1-adamantyl)-N'-(o-nitrophenyl)guanidine (IC$_{50}$=30 nM); N,N'-di-(($\pm$)-endo-2-norbornyl)guanidine (IC$_{50}$=16 nM); N-(exo-2-isobornyl)-N'-(o-iodophenyl)guanidine (IC$_{50}$=18 nM); N,N'-di-(exo-2-norbornyl)guanidine (IC$_{50}$=22 nM); N-(exo-2-isobornyl)-N'-(o-tolyl)guanidine (IC$_{50}$=25 nM); N-(o-iodophenyl)-N'-(t-butyl)guanidine (IC$_{50}$=20 nM); N,N'-dibenzylguanidine (IC$_{50}$=90 nM); N-(adamant-1-yl)-N'-(o-isopropylphenyl)guanidine (IC$_{50}$=24 nM); N-(adamant-1-yl)-N'-(p-bromo-o-tolyl)guanidine (IC$_{50}$=2.7 nM); N-(cyclohexyl)-N'-(p-bromo-o-tolyl)-guanidine (IC$_{50}$=5.5 nM); and N-(adamant-2-yl)-N'-(o-iodophenyl)guanidine (IC$_{50}$=5.2 nM).

A preferred class of N,N-disubstituted guanidines have saturated or unsaturated alkylene groups substituted between the nitrogen of the guanidine and a cyclic group. Such N,N'-disubstituted guanidines have the Formula (II):

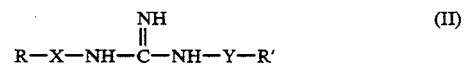

wherein
X and Y are independently a branched or straight chain C$_1$–C$_{12}$ alkylene or a branched or straight chain C$_2$–C$_{12}$ alkylene or wherein one of X and Y is a single bond;
R and R' are independently hydrogen, a cycloalkyl group of at least 3 carbon atoms, a carbocyclic aryl group of at least 6 carbon atoms, alkaryl or aralkyl of at least 6 carbon atoms and containing 1–3 separate or fused rings, a heterocyclic ring, and wherein each of R and R' may be substituted in 1–3 positions, or wherein R and R' together with the guanidine group to which they are attached form a saturated or unsaturated cyclic ring containing at least 4 carbon atoms exclusive of the guanidine carbon atom, and wherein said cyclic ring may be substituted with one or more alkyl groups of 1–6 carbon atoms, carbocyclic aryl groups of at least 6 carbon atoms, cycloalkyl groups of 3–12 carbon atoms, or 1–2 fused aromatic rings, and further wherein said N,N'-disubstituted guanidine exhibits a high affinity for the sigma receptor.

Preferably, X and Y are C$_1$–C$_4$ alkylene groups.

A second preferred class of N,N'-disubstituted guanidines have the following Formula (III):

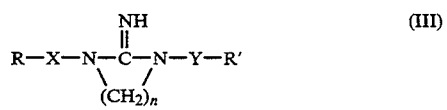

wherein
n is 2, 3, 4 or 5;

X and Y are independently a single bond, a branched or straight chain $C_1$–$C_{12}$ alkylene or a branched or straight chain $C_2$–$C_{12}$ alkylene;

R and R' are independently hydrogen, a cycloalkyl group of at least 3 carbon atoms, a carbocyclic aryl group of at least 6 carbon atoms, aralkyl of at least 6 carbon atoms and containing 1–3 separate or fused rings, a heterocyclic ring, and wherein each of R and R' may be substituted in 1–3 positions, or wherein R and R' together with the guanidine group to which they are attached form a saturated or unsaturated cyclic ring containing at least 4 carbon atoms exclusive of the guanidine carbon atom, and wherein said cyclic ring may be substituted with one or more alkyl groups of 1–6 carbon atoms, carbocyclic aryl groups of at least 6 carbon atoms, cycloalkyl groups of 3–12 carbon atoms, or 1–2 fused aromatic rings, and further wherein said N,N'-disubstituted guanidine exhibits a high affinity for the sigma receptor.

Preferably, R and R' are o-tolyl, X and Y are single bonds and n is 2, e.g., N,N'-di(o-tolyl)-2-iminoimidazolidine.

The level of sigma receptor activity of the disubstituted guanidines can also be determined in vivo in a discriminative stimulus property test employing rats trained to discriminate between intraperitoneal injections of cyclazocine (2.0 mg/kg) and saline in a discrete-trial avoidance paradigm with sessions of 20 trials each. For example, ditolylguanidine (DTG) and diphenylguanidine (DPG) were fully substitutable for cyclazocine at the same concentrations. (Holtzman, S. G., Emery University, Atlanta, Ga., private communication.)

Although the discussion hereinafter of the experiments below relates to certain of these selective sigma receptor ligands, viz., the N,N'-disubstituted guanidines of Table I below, the activity and utility of that compound apply comparably to the other disubstituted guanidines which compete with and displace in vitro N,N'-di-(4-[$^3$H]-2-methylphenyl)-guanidine bound in vitro to isolated guinea pig brain membrane.

In carrying out the sigma receptor binding activity measurement method of this invention, a known amount of a mammalian brain membrane, e.g., human or other primate, porcine, rodent, e.g., rat or guinea pig, which has SKF 10,047 and like psychotomimetic benzomorphan binding activity is contacted in a suitable aqueous vehicle, e.g., physiological saline solution, with a mixture, usually in a solution in a suitable aqueous vehicle of (i) a tritium-labeled N,N'-di-substituted guanidine of this invention having sigma receptor binding activity, in an amount capable of being fully bound to the abovesaid amount of membrane and (ii) a water soluble organic compound whose sigma receptor activity is to be assayed, in known amounts, sufficiently varied to obtain a dose-response curve. The techniques for obtaining a dose-response curve are standard and well known to those skilled in the art. Typically, one could employ molar amounts varying as much as from $10^{-4}$ to $10^4$ of the molar amount of the tritium labeled compound present in the mixture, e.g., employing from 10 to 120 and preferably 30 to 90 such mixtures.

If the organic compound being assayed has sigma receptor binding activity, a portion of the tritium labeled compound which, in the absence of the organic compound would bind to the membrane remains unbound and is thus separable from the membrane. The amount which remains unbound is proportional to the sigma receptor binding activity of the organic compound and the molar ratio thereof in the mixture to the tritium labeled compound.

The two compounds can be employed at any convenient collective concentration, e.g., from $10^{-8}$ to $10^3$ mM.

In the next step, the membrane is separated from and washed until free of the solution in which step (a) is conducted. In the next step, the amount of tritium labeled compound which is thus separated from the membrane is determined, e.g., by measuring the collective radioactivity level of the separated solution and wash water and comparing that radioactivity to that obtained when the foregoing steps are conducted with the same amount of tritium-labeled N,N'-di-substituted guanidine in the absence of the organic compound.

In the next step of the method, the activity of sigma receptor binding activity of the organic compound is determined from the dose response curve thus obtained.

All of the foregoing steps are conventional and have been employed in the prior art with other types of $^3$H-labeled compounds having sigma receptor binding activity. The method of this invention is, however, unique in that the tritium-labeled N,N'-disubstituted guanidines of this invention are highly selective to binding by the sigma receptors and therefore will not compete with organic compounds which bind to other brain receptors.

In carrying out the method of treatment aspect of this invention, e.g., treating a human being suffering from a psychotic mental illness associated with hallucinations there is administered thereto a water-soluble N,N'-disubstituted guanidine which is an antagonist to the sigma receptor binding activity of a hallucinogenic benzomorphan, in an amount effective to ameliorate the hallucinations. Preferably, the guanidine is a compound of Formulae I, II or III wherein R and R' each is an alkyl group of at least 4 carbon atoms, a cycloalkyl group of 3 to 12 carbon atoms or a carbocyclic aryl group of at least 6 carbon atoms. In preferred aspect, the human being is schizophrenic; in another preferred aspect, the compound is N,N'-di-(2-methylphenyl)-guanidine, N-(adamantyl)-N'-(cyclohexyl)guanidine, N-adamantyl-N'-(2-methylphenyl)guanidine, N-(1-adamantyl)-N'-(o-iodophenyl)guanidine, N-(2-adamantyl)-N'-(o-iodophenyl)guanidine, N-cyclohexyl-N'-(2-methylphenyl)guanidine, N,N'-di-(cyclohexyl)guanidine, N,N'-di-(2-adamantyl)guanidine, N,N'-di-(m-n-propylphenyl)guanidine, N-(o-tolyl)-N'-(p-nitro-o-tolyl)guanidine, N,N'-di-(1-tetralinyl)guanidine, N-(o-tolyl)-N'-(o-xylyl)guanidine, N,N'-di-(o-xylyl)guanidine, N-(3,5-dimethyl-adamantan-1-yl)-N'-(o-tolyl)-guanidine, N-(3,5-dimethyladamantan-1-yl)-N'-(o-iodophenyl)guanidine, N-(1-adamantyl)-N'-(o-nitrophenyl)-guanidine, (+) and (−)N-(exo-2-norbornyl)-N'-(2-iodophenyl)guanidine, (+) and (−)N-(endonorbornyl)-N'-(o-tolyl)guanidine, (+) and (−)N-(exonorbornyl)-N'-(o-tolyl)guanidine, (+) and (−)N,N'-di(endonorbornyl)guanidine, (+) and (−)N-(exoisobornyl)-N'-(o-iodophenyl)guanidine, (+) and (−)N,N'-di-(exonorbornyl)guanidine, N-(o-iodophenyl)-N'-(t-butyl)-guanidine, N,N'-dibenzylguanidine, N-(adamant-1-yl)-N'-(o-isopropylphenyl)guanidine, N-(adamant-1-yl)-N'-(p-bromo-o-tolyl)guanidine, N-(cyclohexyl)-N'-(p-bromo-o-tolyl)guanidine, N-(adamant-2-yl)-N'-(p-iodophenyl)-guanidine, N,N'-di(o-methylbenzyl)guanidine and N,N'-di(1-adamantanemethyl)guanidine; or a corresponding compound bearing 1, 2, 3 or more additional or other substituents on one or both hydrocarbon groups, e.g., alkyl of 1-8 carbon atoms, e.g., methyl-, ethyl; halo, e.g., chloro, bromo, iodo, fluoro; nitro; azido; cyano; isocyanato; amino; lower-alkylamino; di-lower-alkylamino; trifluoromethyl; alkoxy of 1-8 carbon atoms, e.g., methoxy, ethoxy and propoxy; acyloxy, e.g., alkanoyloxy of 1-8 carbon atoms, e.g., acetoxy and benzoyl; amido, e.g., acetamido, N-ethylacetamido; carbamido, e.g., carbamyl, N-methyl-carbamyl, N, N'-dimethyl carbamyl; etc.

N,N'-disubstituted guanidines, e.g., of Formulae I and II, can act in an agonistic, antagonistic or inverse agonistic manner in relation to the prototypical sigma benzomorphans. Those which act as antagonists can therefore be expected to affect pupil size, heart rate and mentation in a direction opposite that caused by benzomorphans which can be determined by standard tests in laboratory animals. The type and level of activity for a given dosage of each compound can be conventionally determined by routine experimentation using well known pharmacological protocols for each of the activities; the corresponding indications treatable at that dosage will be well known to skilled workers based on the pharmacological results. The compounds of this invention are particularly noteworthy for their antipsychotic activity to treat psychotic conditions, e.g., schizophrenia, by analogy to the known agents prolixin and haloperidol and for diagnosing sigma receptor intoxicated conditions. The [$^3$H]DTG of this invention is useful as a screening tool for compounds, such as the disubstituted guanidines of this invention, which are selective ligands for the sigma receptor binding site. As such, they are useful for screening for compounds useful for the diagnosis and treatment of sigma receptor mediated hallucinogenic mental disorders. For example, such a compound which is an agonist to a putative natural ligand will temporarily exacerbate such a mental disorder which is the result of an overabundance of the endogenous ligand and will ameliorate a mental disorder which is the result of an abnormal insufficiency of the natural ligand. The converse occurs when the disubstituted guanidine is an antagonist to the putative endogenous ligand. In either case, the temporary alteration of the mental disorder by the administered ligand confirms that it is a sigma receptor associated disease, thereby eliminating other possible causes thereof, e.g., chemical toxicity, and facilitating the treatment thereof.

[$^3$H]-DTG also binds to human brain membrane receptors with high affinity as determined in our laboratory. Therefore another use of [$^3$H]-DTG is to explore the neurochemistry of mental disease by measuring the fluctuations in receptor density or function in postmortem tissue of patients manifesting psycho- or neuropathology as contrasted with tissue from normals (unaffected controls). This topic can be studied by both receptor binding assays and autoradiography.

The N,N'-disubstituted guanidines can readily be prepared by conventional chemical reactions, e.g., when R and R' are the same, by reaction of the corresponding amine with cyanogen bromide. Other methods which can be employed include the reaction of an amine with a preformed alkyl or aryl cyanamide. See Safer, S. R., et al., *J. Org. Chem.* 13:924 (1948). This is the method of choice for producing N,N'-disubstituted guanidines in which the substituents are not identical. For a recent synthesis of unsymmetrical guanidines, see G. J. Durant et al., *J. Med. Chem.* 28:1414 (1985), and C. A. Maryanoff et al., *J. Org. Chem.* 51:1882 (1986), incorporated by reference herein.

Included as well in the present invention are pharmaceutical compositions comprising an effective amount of the N,N'-disubstituted guanidines in combination with a pharmaceutically acceptable carrier.

The N,N'-disubstituted guanidines and the pharmaceutical compositions of the present invention may be administered by any means that achieve their intended purpose. For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

Compositions within the scope of this invention include all compositions wherein the N,N'-disubstituted guanidine is contained in an amount which is effective to achieve its intended purpose. While individual needs vary, determination of optimal ranges of effective amounts of each component is with the skill of the art. Typically, the N,N'-disubstituted guanidine compounds may be administered to mammals, e.g. humans, orally at a dose of 0.0025 to 15 mg/kg, or an equivalent amount of the pharmaceutically acceptable salt thereof, per day of the body weight of the mammal being treated. Preferably, about 0.01 to about 10 mg/kg is orally administered to treat or prevent such disorders. For intramuscular injection, the dose is generally one-half of the oral dose. For example, for treatment or prevention of psychosis, a suitable intramuscular dose would be about 0.0025 to about 15 mg/kg, and most preferably, from about 0.01 to about 10 mg/kg.

The unit oral dose may comprise from about 0.25 to about 400 mg, preferably about 0.25 to about 100 mg of the N,N'-disubstituted guanidine compound. The unit dose may be administered one or more times daily as one or more tablets each containing from about 0.10 to about 300, conveniently about 0.25 or 50 mg of the N,N'-disubstituted guanidine compound or its solvates. In addition to administering the compound as a raw chemical, the compounds may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 0.25 to 75 percent of active compound(s), together with the excipient.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tri-calcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, steric acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers.

The characterization of sigma receptors in vitro has been difficult because of the lack of selective drug ligands. Most benzomorphan opiates cross-react with other (mu, delta, kappa), opioid receptors and are therefore of only limited value for characterizing and isolating receptors. Pasternak et al., *J. Pharmacol. Exp. Ther.* 219:192–198 (1981); Zukin, R. S., et al., *Mol. Pharm.* 20:246–254 (1981); and Tam, S. W., *Eur. J. Pharmacol.* 109:33–41 (1985). [$^3$H]DTG binds specifically and with high affinity to a single class of binding sites in guinea pig brain membranes. The binding characteristics and the drug specificity profile of these sites are concordant with those proposed for the sigma receptor, including 1) naloxone insensitivity and stereoselectivity for dextrorotatory isomers of benzomorphan opiates such as (+)SKF 10,047, (+)cyclazocine and (+)pentazocine; 2) high affinity for haloperidol and certain phenothiazine antipsychotic drugs; 3) stereoselectivity for (−)butaclamol; and 4) insensitivity to dopamine and apomorphine. [$^3$H]-DTG is one of only two known tritiated compounds that are selective for the sigma site. The other, (+)[$^3$H]3PPP, originally proposed to be a dopamine autoreceptor agonist, has recently been shown to be selective for sigma sites in rat brain membrane binding assays. Largent et al. (1984), supra. Our experiments confirm these findings in the guinea pig and show that [$^3$H]DTG and (+)[$^3$H]3-PPP have virtually identical receptor binding characteristics and drug selectivity profiles. Previous studies have shown that sigma sites can also be labeled with (+)[$^3$H]SKF 10,047, (+)[$^3$H]-ethylketazocine and with (±)[$^3$H]SKF 10,047. However, these ligands are not selective for the sigma site and require the presence of appropriate drugs in the binding assays to mask cross-reacting non-sigma binding sites.

[$^3$H]DTG has a number of advantages as a sigma ligand. It is highly selective for the sigma site (unlike [$^3$H]SKF 10,047 and (+)[$^3$H]ethylketazocine), it has a high degree of specific binding (90–97% of total binding) and it has a relatively simple chemical structure that is not chiral (unlike (+)[$^3$H]3-PPP and the benzomorphan opiates). These characteristics make it a good starting compound for the synthesis of analogs for structure-activity studies and for the design of irreversible (after photolysis) sigma receptor ligands, e.g., compounds of Formulae I and II wherein at least one of R and R' is azido-substituted carbocyclic aryl.

The sigma site labeled with [$^3$H]DTG is clearly not related to conventional (mu, delta, kappa) opioid receptors as it is naloxone insensitive and shows stereoselectivity for dextrorotatory isomers of benzomorphan drugs. This is a reversed stereoselectivity compared to naloxone-sensitive opioid receptors which are selective for levorotatory isomers of opiates. Sigma receptors should therefore not be referred to as sigma "opioid" receptors. The drug selectivity of sigma sites for dextrorotatory isomers of psychotomimetic opiates does, however, correlate well with the pharmacological profile of dextrorotatory versus levorotatory opiates in animal tests designed to differentiate between conventional opioid receptor activity and sigma (behavioral) activity of benzomorphan drugs. Cowan, A., *Life Sci.* 28:1559–1570 (1981); Brady, K. T., et al., *Science* 215:178–180 (1982); and Khazan, N., et al., *Neuropharmacol.* 23:983–987 (1984).

Autoradiography studies using [$^3$H]DTG visualize the sigma site in slide-mounted rodent brain sections and confirm that sigma sites are different from mu, delta, and kappa opioid receptors as the distribution of [$^3$H]DTG binding is rather distinct from the distribution of mu, delta, kappa opioid receptors. The anatomical distribution of [$^3$H]DTG binding sites is, however, very similar if not identical to the distribution of [3H]3-PPP binding sites, further confirming that the two radioligands label identical binding sites. The high affinity of the [3H]DTG binding site for haloperidol and for certain phenothiazine antipsychotics (TABLE I) which are also dopamine $D_2$ receptor antagonists raises the question as to the relation of sigma receptors to dopamine $D_2$ receptors. The results presented show that the [3H]DTG site is clearly distinct from dopamine $D_2$ receptors, because the autoradiographic distribution of dopamine receptor is dissimilar and because dopamine, apomorphine and many other dopamine receptor ligands do not interact with the [3H]DTG binding site.

Furthermore the sigma site labeled with [3H]DTG is stereoselective for (−)butaclamol which is a reversed stereoselectivity compared to the dopamine $D_2$ receptors which are stereoselective for (+)butaclamol.

The haloperidol-sensitive sigma site labeled with [3H]DTG was found to have a moderate affinity for the potent hallucinogen PCP in competition experiments. This is in agreement with findings by others who use (+)[3H]SKF 10,047, (±)[3H]SKF 10,047 or (±)-[3H]3-PPP to label sigma sites. In PCP receptor binding assays, however, [3H]-PCP labeled predominantly (but not exclusively) a haloperidol-insensitive PCP binding site, termed PCP/sigma opiate receptor by Zukin and colleagues, Zukin et al. (1981, 1986), supra, which is separate from the haloperidol-sensitive sigma site labeled with [3H]DTG or (+)[3H]3-PPP. In contrast, [3H]DTG appears to label exclusively the haloperidol sensitive sigma site, since all specific binding is displaceable by haloperidol and the anatomical distribution of [3H]DTG binding is distinct from the distribution of PCP receptors. Furthermore, unlabeled DTG is virtually inactive in a [3H]-PCP binding assay (S. William Tam, E.1. DuPont De Nemours & Co., Wilmington, Del., personal communication). There is some controversy as to which of the two binding sites is responsible for causing the behavioral effects of PCP and psychotomimetic benzomorphan opiates and would therefore correspond to the sigma receptor postulated by Martin et al. (1976), supra. Zukin and his collaborators have argued that the behavioral effects of both PCP and psychotomimetic benzomorphan opiates are mediated by the haloperidol-insensitive PCP site, to which benzomorphan opiates bind with moderate affinity. Largent et al. (1986), supra, cited circumstantial evidence suggesting that it is equally likely that the behavioral effects of both PCP and psychotomimetic opiates are mediated through the haloperidol sensitive sigma site. As [3H]DTG exclusively labels the haloperidol sensitive sigma site and does not interact significantly with the haloperidol-insensitive PCP site, behavioral studies using DTG or other substituted guanidines of this invention as prototypical sigma ligands, taking into account of whether they are agonists or antagonists (see below), should resolve this issue.

Perhaps the most important aspect of the findings on the drug specificity of sigma sites that have emerged from this and other studies is that they interact with certain very potent antipsychotic drugs (haloperidol, phenothiazines) that are used clinically to treat schizophrenia. This intriguing drug selectivity profile facilitates studies aimed at investigating the role of sigma receptors in antipsychotic drug action and abnormal brain function. The availability of DTG and like N,N'-disubstituted guanidines as a selective sigma ligand should serve to facilitate such studies.

The compounds of this invention have highly selective affinity for the sigma receptor. Consequently, they may have some of the activities of the benzomorphans, i.e., those produced by binding to the haloperidol-sensitive sigma receptor but not those produced by the binding of benzomorphans to other non-sigma receptors. For instance, benzomorphans may act at sigma receptors to cause mydriasis and tachycardia and pronounced psychotomimetic effects. DTG is therefore an effective tool to demonstrate the physiological effects mediated by the sigma receptor which, to date, have been obscured by cross-reactivity of benzomorphans with non-sigma receptors. Additionally, at least some of the compounds of Formulae I and II, e.g., N,N'-diphenyl and N,N'-di-o-tolyl-guanine, are antagonists of the sigma receptors in the nerve terminals in the mouse vas deferens, where sigma receptors stimulate noradrenaline release (a phenomena discovered by us and which provides a new screening test for CNS-stimulants and depressants), and thus are blood pressure lowering (antihypertensive) agents.

The compounds of this invention are particularly valuable in the treatment of humans afflicted with a psychotic disease, e.g., schizophrenia, or with chronic hypertension. In this regard, they can be employed in substantially the same manner as known antipsychotic agents and anti-hypertensive agents, respectively.

It will be appreciated that the actual preferred amounts of active compounds used will vary according to the specific compound being utilized, the particular compositions formulated, the mode of application, and the particular site of administration, as well as the age, general health, and concurrent treatment of the patient. Optimal administration rates for a given protocol of administration can be readily ascertained by those skilled in the art using conventional dosage determination tests conducted with regard to the foregoing guidelines.

The sigma receptor binding activity of N,N'-di-o-tolyl-guanidine (DTG) was discovered during studies on the purification and characterization of an endogenous sigma receptor ligand. In the initial phases of this work numerous extraction solvents were tested for their suitability to extract endogenous sigma receptor ligand from cow brains. Certain extraction solvents (particularly acetone) contained an unidentified material that potently displaced (+)-[3H]SKF 10,047 from guinea pig brain membrane binding sites. A receptor binding characterization of the material revealed that the binding activity was competitive, reversible and rather potent. Because of the potent sigma receptor binding properties of three compounds that were found in these solvents, these chemicals were purified to homogeneity using various reverse phase HPLC procedures and their structure determined. Their structure was determined by a combination of different methods including high resolution mass spectroscopy, nuclear magnetic resonance and UV-spectrophotometry. One of the three sigma receptor ligands proved to be 1,3-di-o-tolyl-guanidine (DTG).

After its structural characterization, synthetic DTG was tested in the (+)-[3H]SKF 10,047 binding assay and was found to displace (+)[-3H]SKF 10,047 from its brain membrane binding sites with a $K_d$ of 70 nM. The displacement was competitive and fully reversible.

Two other compounds were isolated and characterized and concluded to be di-phenyl-guanidine (DPG)

and dibutyl-guanidine (DBG). Both compounds were active in the (+)-[³H]SKF 10,047 binding assay.

Because of the high potency of DTG and related disubstituted guanidines to displace (+)-[³H]-SKF 10,047 from its binding sites it was decided to synthesize a tritium labeled derivative of DTG. To do so, N,N'-di-(2-methyl-4-bromo-phenyl)-guanidine was subjected to catalytic reduction with tritium gas, which replaced the two bromine atoms with tritium atoms to produce N,N'-di(p-[³H]-o-tolyl)-guanidine, as described below.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. The entire text of all applications, patents and publications, if any, cited above and below are hereby incorporated by reference.

EXAMPLES

In the foregoing and in the following examples, all temperatures are set forth uncorrected in degrees Celsius and unless otherwise indicated, all parts and percentages are by weight.

Preparations

General Procedures. Melting points are uncorrected. NMR spectra were recorded on a General Electric QE-300 spectrometer, operating at 300 MHz. Chemical shifts ($\delta$) are given in ppm using the residual proton signal of the deuterated solvent as reference ($CHD_2OD$ $\delta 3.300$, $CHCl_3$ $\delta 7.260$, $HDO$ $\delta 4.80$), or the $^{13}C$ signal of the solvent ($CD_3OD$ $\delta 49.00$, $CDCl_3$ $\delta 77.00$). All solvents were reagent grade quality. Where dry solvents were needed, these were distilled from $CaH_2$ or Na before use.

Adamantan-1-ylcyanamide was prepared from the amine with cyanogen bromide in $Et_2O$, as previously described by Geluk, N .W., et al., *J. Med. Chem.* 12:712–716 (1969). (2-Methylphenyl)cyanamide was prepared similarly.

N,N'-Di-(adamantan-1-yl)guanidine hydrochloride was prepared according to the procedure of Geluk et al., supra.

Example 1

N,N'-Di-(4-bromo-2-methylphenyl)-guanidine (4-Br-DTG)

To a stirred solution of cyanogen bromide (846 mg, 8.06 mmol) in distilled water (70 ml) was added in small portions 2.997 g (16.11 mmol) of 4-bromo-2-methylaniline (Aldrich, recrystallized from etherpentane). A white precipitate formed during the addition. The mixture was stirred at 80° C. for 4 h. Upon cooling at 0° C. for 12 h, a sticky yellow oil separated out and was discarded. The clear aqueous phase was concentrated to about 30 ml. The white precipitate which formed was redissolved by heating the mixture. This was then set aside at 4° C. for 12 h. Filtration gave 430 mg of white solid. A 200-mg portion was dissolved in 10 ml of hot water and treated with 5 ml of 10 KOH solution. The mixture was extracted with $CHCl_3$ and the extract was washed with brine and then dried ($MgSO_4$). Evaporation of the solvent gave 171 mg of a brown solid which was crystallized from $CHCl_3$, giving 120 mg (8%) 4-Br-DTG as small white needles: mp 209°–210°; NMR (300 MHz, $CD_3OD$, TMS) $\delta 2,24$ (s, 3), 7.12–7.25 (AB, 2, J=8 Hz), 7.35 (s,1); IR (KBr) 3460, 3340, 1630 cm$^{-1}$.

Analysis calculated for $C_{15}H_{15}N_3Br_2$: C, 45.37; H, 3.81; N, 10.58. Found: C, 45.34; H, 3.56; N, 10.50.

Example 2

[³H]-N,N'-di-ortho-tolyl-guanidine ([³H]DTG)

Twenty-five mg (0.1 mmol) of the thus-produced 4-Br-DTG were submitted to Amersham Corporation (Arlington Heights, Ill.) for catalytic reduction in the presence of 20 Ci of [³H]-gas. Two mCi portions of the crude, radioactive product in 0.2 ml/each of 25% ethanol were purified by reverse phase high performance liquid chromatography (RP-HPu) on a Vydac TP218 octadecasilica column using a $CH_3OH$ gradient (0–35% in 60 minutes) in 0.1% trifluoroacetic acid for elution. Flow rate was 1 ml/min. One minute fractions were collected. Aliquots of the fractions were diluted 100 fold and 10 ul aliquots of the diluted fractions corresponding to 0.1 ul of the original fractions were dissolved in 10 ml scintillation fluid and counted in a scintillation spectrometer. The equipment consisted of 2 Waters HPLC pumps, and automated electronic gradient controller and a Kratos variable wave length spectrophotometer. The radioactivity eluted as a major symmetrical peak coinciding with a major, symmetrical UV (220 nm) absorbing peak at 41 minutes. This is the same elution time at which authentic, unlabeled DTG emerges from the column in this RP HPLC system. The specific activity of [³H]DTG was found to be 52 Ci/mmol based on the amount of DTG under the major UV absorbing peak as determined by quantitative UV-spectrophotometry and the amount of radioactivity associated with this peak as determined by quantitative liquid scintillation spectrometry.

Following this procedure, or one of another conventional labelling synthetic techniques well known in the art, the tritium labeled versions of other N,N'-disubstituted guanidines of this invention, e.g., those of Table I, can be produced. If only one of the N- and N'-groups employed as starting material bears a functional group convertible to an [³H] bearing group, the resulting N,N'-disubstituted guanidine will be singly tagged. If both bear such a functional group, the resulting N,N'-disubstituted guanidine will be polytagged.

Example 3

N-(2-Methyl-4-isothiocyanatophenyl-N'-[2-methylphenyl)-guanidine [Di-toyl-Guanidine-Isothiocyanate (DIGIT)]

a.

N-(2-Methyl-4-nitrophenyl)-N'-(2-methyl-phenyl)-guanidine Hydrochloride and the corresponding free base A vigorously stirred mixture of 2-methylphenylcyanamide [1.107 g, 0.380 mmol, prepared from o-toluidine by the method of Safter et al. (1948)] and 2-methyl-4-nitroaniline hydrochloride in chlorobenzene (45 ml) was heated at 90° for 3 h and then allowed to cool to 25°. The resulting pale yellow precipitate was collected, washed with $CH_2Cl_2$ and dried, giving 2.284 g (91%) of the hydrochloride of the desired product (pure by NMR). A 681 mg sample was recrystallized twice from absolute EtOH to give 600 mg (88%) of the desired product as pale yellow microcrystals suitable for the next reaction: mp 196–200; ($CD_3OD$, 300 MHz) 2.37 (s, 3), 2.47 (s, 3), 7.33–7.40 (m, 4), 7.59 (d, 1), 8.18 (dd, 1), 8.27 (d, 1). A 473 mg sample of the hydrochloride was dissolved in 50 ml of hot water, filtered, cooled to 25°, and treated with 5 ml of 5 N NaOH. The resulting bright yellow precipitate of the title compound (free base) was dried (403 mg, 92%) and then recrystallized twice from 95% EtOH to give the analytical sample as yellow platelets: mp 177–179; (DC$_3$OD, 300 MHz) 2.31 (s, 6), 7.01–7.35 (m, 5), 7.98 (dd, 1), 8.06 (d, 1). Analysis calculated for C$_{15}$H$_{16}$N$_4$O$_2$:C, 63.37; H, 5.67; N, 19.71. Found: C, 63.41; H, 5.42; N, 19.90.

b.
N-(2-Methyl-4-aminophenyl)-N'-(2-methylphenyl)-guanidine hydrochloride

A Parr hydrogenation flask was charged with a solution of N-(2-methyl-4-nitrophenyl)-N'-2-(methylphenyl)-guanidine hydrochloride (478 mg) in 30 ml of absolute EtOH. 30% Pd on charcoal (71 mg) was added and then the mixture was hydrogenated at 60 psi at 25° C. for 12 h. All further operations were carried out under an atmosphere of Ar. The mixture was centrifuged, filtered through Celite and the filtrate was concentrated in vacuo to 2 ml. Ether (21 ml) was added and after 4 h at 20°, the white precipitate was collected and dried, giving 406 mg (78%) of the title compound (amine hydrochloride) suitable for the next reaction: mp 232.5°–234.5°, (CD$_3$OD, 300 MHz) δ2.22 (s, 3), 2.34 (s, 3), 6.60 (dd, 1), 6.66 (d, 1), 6.98 (d, 1), 7.26–7.38 (m, 4).

c.
N-(2-Methyl-4-isothiocyanatophenyl)-N'-(2-methylphenyl)guanidine Hydrochloride (DIGIT)

NaOAc (1.767 g, 21.5 mmol) and HOAc (0.839 g, 14.0 mmol) were dissolved in dry MeOH such that the final volume of the solution was 100 ml. A 12.7 ml aliquot of this solution was added to 199 mg (0.686 mmol) of N-(2-methyl-4-aminophenyl)-N'-(2-methylphenyl)-guanidine hydrochloride under an Ar atmosphere. Thiophosgene (54.7 ul, 86.7 mg, 0.754 mmol, freshly distilled) was then injected into the stirred reaction mixture. The reaction was complete upon mixing as judged by silica gel TLC (500:100:1, CHCl$_3$-MeOH-HOAc). Water (20 ml) was added and the mixture was concentrated in vacuo to 19 ml.

The next steps were done in rapid succession in order to minimize the possible reaction of the isothiocyanate group with the guanidine free base grouping of another molecule. The above 19 ml concentrate was cooled to 0° and treated with ice-cold saturated NaHCO$_3$ (15 ml). The resulting mixture containing a white precipitate was extracted with CHCl$_3$ (4×15 ml). The combined extracts were washed with ice cold brine, dried (MgSO$_4$), filtered through Celite, and cooled to 0°. Next, excess HCl gas was bubbled through the colorless solution then the solution was concentrated in vacuo to 25 ml and hexane (20 ml) was added. Four additional times the mixture was concentrated again and more hexane was added. Evaporation of the final mixture dryness gave crude hydrochloride as a gummy white solid (263 mg, 115%). This was taken up in absolute ethanol (2 ml), and diluted with ether (80 ml) to give a cloudy white suspension from which small clusters of white needles formed on standing. The crystals were centrifuged, washed with ether (3×5 ml), and dried, giving 173 mg (76%) of the title compound: m.p. 195°–197° C. (preheated bath); (CD$_3$OD), 300 MHz) δ2.347 (s, 3), 2.351 (s, 3), 7.23 (d, 1), 7.31 (s, 1), 7.34 (d, 1), 7.26–7.40 (m, 4); IR (KBr) 3466, 3138, 2927, 2152, 2119, 1646, 1631 cm$^{-1}$. Analysis calculated for C$_{16}$H$_{17}$ClN$_4$S: C, 57.74; H, 5.15; N, 16.83. Found: C, 57.60; H, 5.20; N, 16.64.

A tri-tritiated version of DIGIT is prepared starting with tritiated N-(2-methyl-4-aminophenyl)-N'-(2-methylphenyl)-guanidine, which was prepared by catalytic tritiation (Amersham) of N-(2-methyl-4-nitro-6-bromophenyl)-N'-(2-methyl-4,6-dibromophenyl)-guanidine. The tri-tritiated amino compound was also used as the immediate precursor for the preparation of the tri-tritiated version of the 4-azido compound the preparation of which is described hereinafter and which was used in the solubilization of sigma receptors.

Example 4
N-adamantan-1-yl-N'-cyclohexylguanidine-HCl

Adamantan-1-yl-cyanamide (514 mg, 2.92 mmol), and cyclohexylamine hydrochloride (398 mg, 2.93 mmol) were finely ground together, and heated at 200° C. for 10 min. The resultant glassy solid was pulverized, and extracted twice with 50 ml boiling 5% HCl. The insoluble material was filtered, and dried. 346 mg, mp 264°–270° (p.h.b. 240° C.). On cooling the combined aqueous extracts to 25°, a white ppt. formed, and was filtered off, 56 mg. Combined crude yield: 44%. Crystallization of a 50 mg sample of the crude product from EtOH/Et$_2$O afforded white needles (25 mg, mp 269°–271° C. (p.h.b. 240°), lit. 268°–269° C.). $_1$H (CD$_3$OD) 1.208–1.474 (m, 5H), 1.744 (s, 9H), 1.967 (s, 8H), 2.119 (5, 3H), 3.434 (m, 1H), $^{13}$C (CD$_3$OD) (broad band decoupled) 25.55, 26.26, 30.96, 33.74, 36.74, 42.73.

Example 5
N-Cyclohexyl-N'-(2-methylphenyl)quanidine

A suspension of cyclohexylamine hydrochloride (310 mg, 2.28 mmol) and (2-methylphenyl)cyanamide (365 mg, 2.76 mmol) in dry chlorobenzene was heated at 125°–135° for 4 hrs. The solvent was evaporated in vacuo with heating, and the residue partitioned between CH$_2$Cl$_2$ and 20×8 ml 10% HCl. The aqueous extracts were made alkaline to pH 9–9.5, and the white precipitate collected after standing at 4° C. overnight. Two recrystallizations from EtOH/H$_2$O gave 140 mg (22%) of white needles, mp 145°–146°, 1H (CD$_3$OD) 1.149–2.054 (m, 10H), 2.164 (s, 3H), 3.50 (m, 1H), 6.875 (d, 1H, J=7.5 Hz), 6.968 (t, 1H, J=7.5 Hz), 7.118 (t, 1H, J=7.5 Hz), 7.177 (d, 1H, J=7.5 Hz). Anal. Calcd for C$_{14}$H$_{21}$N$_3$: C, 72.69; H, 9.15; N, 18.16. Found: C, 72.72; H, 9.24; N, 18.18.

Example 6
N-(Adamantan-1-yl)-N'-(2-methylphenyl)guanidine

A suspension of adamantan-1-ylcyanamide (151 mg, 0.857 mmol) and o-toluidine hydrochloride (186 mg, 0.857 mmol) in dry chlorobenzene was heated between 100°–130° C. for 4.5 hrs. The chlorobenzene was evaporated in vacuo with heating and the residue (285 mg) taken up in 18 ml of water. A gummy, insoluble material was discarded. On adjusting the aqueous extract to pH 9–9.5, a precipitate formed (194 mg, 71%). Two recrystallizations from EtOH/H$_2$O gave the analytical sample; mp 160°–161°, $^1$H (CD$_3$OD) 1.742 (s, 6H), 2.050 (d, 6H, J=2.4 Hz), 2.029 (s, 3H), 6.956 (j, 1H, J=8.1 Hz), 7.056 (t, 1H, J=8.1Hz), 7.168 (t, 1H, J=7.5 Hz), 7.213 (d, 1H, J=7.5 Hz). Anal. Calcd for C$_{18}$H$_{25}$N$_3$: C, 76.28; H, 8.89; N, 14.83. Found: C, 76.25; H, 8.86; N, 14.60.

Example 7

N-(Adamantan-1-yl)-N'-(2-iodophenyl)guanidine HCl

Adamantan-1-ylcyanamide (299 mg, 1.70 mmol) and o-iodoaniline hydrochloride (433 mg 1.70 mmol) were finely ground together and heated at 200° for 10 min. The resultant black glassy solid was pulverized, and recrystallized 5 times from EtOH/Et$_2$O. The resultant faintly blue needles (80 mg) were dissolved in 4 ml EtOH, and passed through a short (<1 cm) column packed from bottom to top with Celite, charcoal, activated alumina, and sand. The colorless eluate was then diluted with 5ml Et$_2$O, and allowed to stand in an Et$_2$O diffusion chamber overnight. The white needles were collected by suction filtration, 40 mg, mp 274°–275° C. Addition of another 5 ml Et$_2$O yielded a second crop (31 mg) of identical material. Combined yield: 21%. $^1$H (CD$_3$OD) 1.779 (s, 6H), 2.090 (s, 6H), 2.164 (s, 3H), 7.168 (t, 1H, J=8.1 Hz), 7.388 (d, 1H, J=9.1 Hz), 7.503 (t, 1H, J=7.8 Hz), 8.004 (d, 1H, J=7.8 Hz).

Example 8

N-(2-Methyl-4-azido-phenyl)-N'-(2-methylphenyl)-guanidine

N-(2-Methylphenyl)-N'-(2-methyl-4-aminophenyl)-guanidine dihydrochloride (112 mg, 0.341 mmol) were dissolved in 2 ml H$_2$O and 100 ul conc. HCl (1.2 mmol). The solution was cooled in an ice bath, and a solution of NaNO$_2$ (42 mg, 0.61 mmol) in 450 ul H$_2$O were added. The reaction mixture turned yellow, and was stirred for 45 min before solid NaN$_3$ (43 mg, 0,661 mmol) was added in a single portion. After N$_2$ evolution was caused, a foamy solid (11 mg) was removed and discarded. Solid NaOH (96 mg, 2.41 mmol) was added, and the bright yellow precipitate was extracted with Et$_2$O (3×5 ml). Evaporation of the combined Et$_2$O layers gave a yellow solid which was crystallized from EtOH/H$_2$O: NMR (CD$_3$OD) 2.279 (s, 3H), 2.284 (s, 3H), 6.864 (dd, 1H, J=2.4 Hz, 8.4 Hz), 6.914 (d, 1H, J=2.1 Hz), 7.055 (td, 1H, J=1.8 Hz, 7.2 Hz), 7.136–7.229 (m, 4H).

Example 9

N-(2-Methyl-4-nitro-6-bromophenyl)-N'-(2-methyl-4,6-dibromophenyl)guanidine N-(2-Methyl-4-nitrophenyl)-N'-(2-methylphenyl)-guanidine, as the free base (281 mg, 0.987 mmol) was dissolved in 4 ml MeOH, and cooled in an ice-bath. N-bromosuccinimide (freshly recrystallized from H$_2$O) (531 mg, 2.98 mmol) was added in two portions over 15 min. After 1.5 hrs the brown sludgy reaction mixture was diluted with 4 ml MeOH, and allowed to warm to 25° C. A brown solid was filtered off (266 mg), and crystallized from acetone/H$_2$O, to afford brown needles (2.6 mg, 42%, mp 193°–195° C). Sublimation of a 56 mg sample of these crystals at .01 mm Hg and 170° afforded the analytical sample as a bright yellow amorphous solid (38 mg, mp 210°–213° C). NMR (CD$_3$OD) 2.357 (s, 3H), 2.488 (s, 3H), 7.444 (d, 1H, J=1.5 Hz), 7.669 (d, 1H, J=1.8 Hz), 8.033 (d, 1H, 2.1 Hz), 8.267 (d, 1H, 2.4 Hz). Anal. Calcd for C$_{15}$N$_{13}$Br$_3$N$_4$O$_2$: C, 34.58; N, 2.52; N, 10.75. Found: C, 34.64; N, 2.47; N, 10.65.

Example 10

N,N'-Bis(2-iodophenyl)guanidine

A solution of cyanogen bromide (4.4042 9, 38.2 mmol) and 2-iodoaniline (4.138 g, 18.9 mmol) in H$_2$O (70 ml) was heated at 70°–80° C. for 5 h. The reaction mixture was decanted from an off-white solid (1.90 g ) which was discarded, and the supernatant was heated at the same temperature an additional 16 h. On cooling to 25° C., the title compound precipitated from solution as its hydrobromide salt and was centrifuged off, and dried (500 mg, 10%). This white powder was dissolved in boiling H$_2$O (20 ml), and 5N NaOH (2 ml) was added to the clear solution. The resulting white precipitate (290 mg) was washed with H$_2$O (3×4 ml), and crystallized from 95% EtOH, to give the title compound (119 mg, 39% from the hydrobromide salt) as long white needles: mp 161°–162° C. One further crystallization provided the analytical sample: mp 161°–162° C. Anal. Calcd for C$_{13}$N$_{11}$N$_3$I$_2$: C, 33.72; N, 2.39; N, 9.07. Found: C, 33.80; N, 2.26; N, 8.78. $^1$N NMR: δ6.790 (t, J=7.8 Hz, 2H), 7.304 (t, 3=7.8 Hz, 2H), 7.506 (d, 3=7.8 Hz, 2H), 7.817 (d, 3=7.8 Hz, 2H). IR: 729, 753, 1467, 1502, 1572, 1613, 1647, 3056, 3387.

Example 11

N,N'-Bis(3-methylphenyl)guanidine

Cyanogen bromide (788 mg, 7.44 mmol) was placed in a 25 ml round bottom flask, and m-toluidine (1.89 g, 17.6 mmol) was added dropwise. After the exothermic reaction had subsided, the residue was taken up in CH$_2$Cl$_2$ (20 ml), and was extracted with 5% HCl (5×10 ml). The aqueous extracts were adjusted to pH 10 with 6N NaOH. The resulting precipitate (674 mg, 38%) was filtered off and crystallized from EtOH/H$_2$O to give the title compound (240 mg, 14%) as white needles: mp 105°–106° C. $^1$H NMR: δ2.289 (s, 6H), 6.814 (d, 2H, J=7.5 Hz), 6.939 (d, 2H, J=7.5 Hz), 6.981 (s, 2H), 7.141 (t, 2H, J=7.5 Hz). Anal. Calcd for C$_{15}$H$_{17}$N$_3$: C, 75.28; H, 7.16; N, 17.56. Found: C, 75.42; H, 7.11; N, 17.43.

References

[1]Geluk, H. W., et al., *J. Med. Chem.* 12:712 (1969).
[2]Kazarinova, N. F., et al., Zn. Anal. Khim. 28:1853 (1973); *Chem. Abstr.* 80:97021 (1973).

Example 12

Synthesis of N,N'-Di(o-toyl)-2-imino-imidazolidine a. Synthesis of N,N' Ditolyl oxalodiamide

Oxalyl chloride (32 mmol) in methylene chloride (16 mL) was added dropwise to a solution of o-toluidine (67 mmol) in methylene chloride (4 mL) over a period of 10 min at 4° C. After the exotherm subsided, the solution was removed from the ice bath and stirred at ambient temperature for 2 h. A white precipitate had formed. The precipitate was filtered off, dried, and found to weigh 724.6 mg (90%). The amide and the hydrooxalate salts were partially dissolved in methylene chloride (20 mL) and extracted with 1N HCl (5x, 15 mL). The resultant white suspension was filtered to provide a white solid (61%, mp 103°–104° C). $^1$H NMR (CD$_3$CN/DMSO): 2.259 (6H, s), 7.128–7605 (8H, m). IR (KBr): 1298.7, 1642.9 (amide).

b. Synthesis of N,N' Bistolyl ethylene diamine

The following procedure was adapted from H. C. Brown, *J. Orgy. Chem.* 38:912 (1978). Diborane (5 mmol) in THF was added dropwise to a THF solution of N,N' Ditolyl oxalodiamide (443.0 mg, 1.65 mmol) over 10 min at O° C. After 30 min, the reaction mixture was allowed to stir at ambient temperature for 6 h. Then the solution was refluxed for 3 h. The resulting yellowish solution was allowed to cool to 25° C. The solution was then acidified dropwise with 15% HCl (15 mL) via an additional funnel over 20 min. Gas evolution was noted and a white precipitate had formed. The THF was then distilled off from the water through rotoevaporation at 25° C. The water was then made basic with an excess of NaOH and then extracted with ether. The ether layer was washed with brine, then dried over anhydrous potassium carbonate. The ether layer was then concentrated to dryness to provide a tannish brown liquid. The liquid was immediately taken up again in dry ether. Following this procedure, the solution was made acidic by adding ethereal HCl (10 mL) dropwise. A white solid had formed. This solid was immediately filtered off and dissolved in ethanol (5 mL) and placed into an ether diffusion chamber. After 2 days, white prisms were found (158.1 mg, 30.6%), mp=268°-270° C.

IR (KBr): in comparison with IR of diamide the bands at 1643.8 and 1298.7 had disappeared.

c. Synthesis of N,N' Bistolyl-2-imino-imidazolidine

N,N' Bistolyl ethylene diamine (105.8 mg, .44 mmol) was taken up in EtOH (3 mL) to provide a light purple solution. This solution was then placed in a one-necked round-bottom flask (25 mL) equipped with magnetic stirbar and reflux condenser. To this solution, cyanogen bromide (50 mg, 0.47 mmol) in ethanol (2 mL) was added in a single portion. The resultant reaction mixture was stirred for 1 h. It was noted that the solution turned clear. The solution was then brought to reflux and maintained at that temperature for 16 h. The reflux condenser was then removed, allowing the solvent to evaporate. The reaction mixture was then fused at 150° C. for 30 min to provide a brown solid. This solid was immediately taken up in ethanol (4 mL) and placed into a centrifuge tube. To this solution 1N NaOH was added (8 mL) to provide a "whispy" tan precipitate. After several failed attempts to pellet the precipitate, the solution was simply extracted with chloroform (20 mL). The chloroform was concentrated to dryness to provide a clear oil (108.1 mg, 92.6%).

Example 13

Characteristics of [$^3$H]DTG binding to guinea pig brain membranes

Synthesis of [$^3$H]DTG resulted in a pure homogenous product of high specific radioactivity (52 Ci/mmol). [$^3$H]DTG bound specifically, saturably, reversibly, and with high affinity to guinea pig brain membrane. In a typical experiment with 0.9 nM [$^3$H]DTG (30,000 cpm, 50% counting efficiency) the total binding was 2700 cpm while the nonspecific binding in the presence of 10 uM DTG or 10 uM haloperidol was 50-150 cpm. Routinely, a specific binding to 90-97% of total binding was observed. At room temperature the binding of [$^3$H]DTG reached equilibrium after 60-90 minutes and it was fully reversible after addition of 10 uM unlabeled DTG. Specific binding was linear with tissue concentration between 2-40 mg tissue (original wet brain weight per assay tube). Binding of radioactivity to the glass fiber filters in the absence of membranes was 10-20 cpm. Boiling of membranes at 100° C. for 10 minutes prior to assay almost completely (90%) abolished specific [$^3$H]DTG binding as did treatment of the membranes with trypsin and pronase (0.01 mg/ml for 30 min at room temperature), indicating that protein components are important for the receptors binding ability.

To determine the equilibrium saturation binding of [$^3$H]DTG to guinea pig brain membranes, membranes prepared as described herein were incubated with [$^3$H]DTG at various concentrations from 0.3 nM to 90 nM in 1 ml 50 nM Tris/HCl buffer, pH 7.4, for 120 minutes at room temperature. Values obtained were the mean of quadruplicate determinations.

A Scatchard analysis of the saturation data shows a linear Scatchard plot with an apparent $K_D$ of 28 nM and a maximum number of binding sites (Bmax) of 85 pmol/g brain tissue (original wet weight). Analysis of the binding data with the curve fitting program LIGAND, Munson, P. J., et al., *Anal. Biochem.* 107:220-239 showed high compatibility with a one site binding model.

Example 14

Radioligand Binding Assays

Frozen guinea pig brains (Pel-Freeze, Rogers, AK) were homogenized in 10 volumes (w/v) of 0.32M sucrose using a Polytron homogenizer. The homogenate was spun at 900×g for 10 minutes at 4° C. The supernatant was collected, and spun at 22,000×g for 20 minutes at 4° C. The pellet was resuspended in 10 volumes of 50 mM Tris/HCl buffer, pH 7.4, incubated at 37° C. for 30 minutes and spun again at 22,000×g for 20 minutes at 4° C. The pellet was then resuspended in 10 volumes of 50 mM Tris/HCl buffer, pH 7.4 and 10 ml aliquots of this membrane suspension were stored frozen at −70° C. until used in the binding assay. No effects of prolonged storage (>3 months) of the membranes at −70° C. on sigma receptor number or affinity for [$^3$H]DTG binding were observed.

For radioreceptor assays aliquots of the frozen membrane suspension were thawed and diluted tenfold with 50 nM Tris/HCl buffer, pH 7.4. To 12×75 mm polystyrene or glass test tubes were added 0.8 ml of membrane suspension, 0.1 ml [$^3$H]DTG or (+)[$^3$H]3-PPP for a final concentration of 0.9 nM, and 0.1 ml of unlabeled drugs or buffer. The protein concentration in the 1 ml final incubation volume was 800 ug, corresponding to 32 mg of brain tissue (original wet weight). Nonspecific binding was defined as that remaining in the presence of either 10 uM DTG or haloperidol for both the [$^3$H]DTG and the (+)[$^3$H]3PPP binding. After incubation for 90 minutes at room temperature the membrane suspension was rapidly filtered under vacuum through Whatman GF/B glass fiber filters using a Brandel 48 well cell harvester (Brandel, Gaithersburg, Md.). The filters were washed with 3×5 ml ice-cold 50 nM Tris buffer (pH 7.4 at room temperature). The filters were dissolved in 10 ml each of Cytoscint (Westchem Products, San Diego, Calif.) and radioactivity was measured by liquid scintillation spectrometry at a counting efficiency of 35-50%. Saturation data were evaluated by Scatchard analysis using both the EBDA NcPherson, Ga., *Computer Programs Biomed.* 17:107-114 (1983), and LIGAND Munson, P. J., et al., *Anal. Biochem.* 107:220-239 (1980), data analysis programs on an IBM Personal Computer-AT. IC$_{50}$ values were determined by plotting displacement curves onto semilogarithmic graph paper followed by interpolation or by computerized non-linear least squares curve fitting (Fischer, J. B. et al., *J. Biol. Chem.* 263:2808-2816 (1988).

Utilizing the radioligand binding assay described above, the sigma receptor binding activity based on [$^3$H]DTG displacement activity (IC$_{50}$ value) for the fourteen (14) N,N'-disubstituted guanidine compounds listed in Table I below was determined. The IC$_{50}$ value for each compound is reported in Table I.

TABLE I

| Compound | IC$_{50}$ vs [$^3$H]DTG (nM) |
|---|---|
| N,N'-di-o-tolyl-guanidine | 32 ± 1 |
| N,N'-di-n-butyl-guanidine | 750 ± 33 |
| N,N'-diphenyl-guanidine | 397 ± 21 |
| N,N'-diadamantyl-guanidine | 17 ± 1 |
| N'-adamantyl-N'-2-methylphenyl-guanidine | 8 ± 1 |
| N,N'-di-(2-methyl-4-bromophenyl)guanidine | 37 ± 3 |
| N'-(2-iodophenyl)-N'-(2-methylphenyl)-guanidine | 21 ± 1 |
| N-(2-methyl-4-nitrophenyl)-N'-(2-methylphenyl)-guanidine | 37 ± 5 |
| N,N'-di-(2,6-dimethylphenyl)guanidine | 90 ± 18 |
| N-(2,6-dimethylphenyl)-N'-(2-methylphenyl)-guanidine | 70 ± 3 |
| N-(adamantyl)-N'-(cyclohexyl)guanidine | 13 ± 2 |
| N,N'-di(cyclohexyl)guanidine | 71 ± 7 |
| N-(2-iodophenyl)-N'-(adamantyl)guanidine | 6 ± 5 |
| N-(2-methylphenyl)-N'-(cyclohexyl)guanidine | 13 ± 1 |
| N-(2-methyl-4-azidophenyl)-N'-(2-methylphenyl)-guanidine | 20 ± 1 |

Example 15

Drug Specificity of [$^3$H]DTG Binding

Displacement experiments were performed with drugs that are considered typical sigma ligands, as well as with drugs considered to be prototypical ligands for other neurotransmitter, neuromodulator, and drug receptors. The IC$_{50}$ vs [$^3$H]DTG and vs. [$^3$H]3-PPP results are given in Table II below. These experiments showed that the [$^3$H]DTG binding site is stereoselective for dextrorotatory benzomorphan opiates and for (−)butaclamol; does not significantly interact with drugs that have high affinities for acetylcholine, benzodiazepine, GABA, nor with mu, delta, or kappa opioid receptors; has a high affinity for haloperidol and several drugs belonging to the phenothiazine class of antipsychotics (haloperidol had the highest displacement potency of all drugs tested); and has a moderate affinity for several other classes of psychoactive drugs, which included several tricyclic antidepressants, PCP, and the kappa opioid receptor ligand U50, 488H.

TABLE II

| Drug | IC$_{50}$ vs. [$^3$H]DTG (nM) (±SEM) | IC$_{50}$ vs. (+)[$^3$H]3-PPP (nM) (±SEM) |
|---|---|---|
| Haloperidol | 5 ± 0.3 | 17 ± 1 |
| DTG | 28 ± 1 | 53 ± 9 |
| Perphenazine | 42 ± 10 | 21 ± 3 |
| (+)Pentazocine | 43 ± 2 | 8 ± 3 |
| (−)Pentazocine | 135 ± 3 | 81 ± 1 |
| (±)Pentazocine | 69 ± 1 | ND |
| (+)3-PPP | 76 ± 4 | 33 ± 12 |
| (−)3-PPP | 280 ± 21 | 235 ± 60 |
| (+)Cyclazocine | 365 ± 25 | 47 ± 12 |
| (−)Cyclazocine | 2,600 ± 210 | 1,000 ± 0 |
| Spiperone | 690 ± 21 | ND |
| (−)Butaclamol | 530 ± 49 | 183 ± 5 |
| (+)Butaclamol | 2,150 ± 250 | 2,100 ± 71 |
| (+)SKF 10,047 | 625 ± 88 | 93 ± 5 |
| (−)SKF 10,047 | 4,000 ± 566 | 2,850 ± 390 |
| PCP | 1,050 ± 106 | 1,000 ± 71 |
| U50,488H | 1,350 ± 106 | ND |
| Trifluoperazine | 345 ± 4 | ND |
| Trifluopromazine | 605 ± 67 | ND |

TABLE II-continued

| Drug | IC$_{50}$ vs. [$^3$H]DTG (nM) (±SEM) | IC$_{50}$ vs. (+)[$^3$H]3-PPP (nM) (±SEM) |
|---|---|---|
| Chlorpromazine | 1,475 ± 265 | ND |
| Amitriptyline | 300 ± 7 | ND |
| Imipramine | 520 ± 14 | ND |
| Desipramine | 4,000 ± 566 | ND |
| Nortriptyline | 2,000 ± 640 | ND |
| Guanabenz | 4,600 ± 283 | ND |
| Clonidine | >10,000 | ND |
| Cocaine | >10,000 | ND |

*IC$_{50}$ is the molar concentration of the drug needed to produce half-maximal displacement of [$^3$H]DTG from sigma receptors. This is a direct measure of the sigma receptor binding potency of the drug. ND = not determined.

The above IC$_{50}$s represent the average from 2–4 separate experiments (in triplicate). The following compounds caused no significant displacement at a 10 uM concentration: scopolamine, 5-OH-tryptamine, diazepam, bicuculline, picrotoxin, hexamethonium, dopamine, apomorphine, GABA, gamma-guanidino butyric acid, morphine, DAGO, metorphamide, dynorphin A, [leu$^5$] enkephalin, beta-endorphin, naloxone, guanidino acetic acid, creatine, creatine, 1,1-dimethyl-4-guanidine, methyl-guanidine, beta-guanidino propionic acid and cimetidine.

Example 16

Drug specificity of [$^3$H]DTG binding compared to (+)-[$^3$H]3-PPP binding

Comparing the drug specificity of [$^3$H]-DTG binding with that of (+)[$^3$H]3-PPP in the guinea pig, it was found that (+)[$^3$H]3-PPP bound specifically, saturably (linear Scatchard plot), reversibly and with high affinity to guinea pig brain membranes (K$_D$=30 nm, Bmax=80 pmol/g fresh brain weight). The drug specificity profile of the (+)[$^3$H]3-PPP binding in the guinea pig (Table II) was found to be very similar to that reported in the rat. Largent et al. (1984), supra. Moreover, the drug specificity profiles of typical sigma receptor active drugs in the (+)[$^3$H]3-PPP and [$^3$H]-DTG binding assays were highly correlated (r=0.95; p≦0.00001) which is consistent with the two compounds labeling the same sites.

Example 17

Autoradiography Studies

Male Sprague Dawley rats (200–250g) and NIH guinea pigs (300–350g) were sacrificed, their brains rapidly removed and processed for receptor autoradiography according to the method of Herkenham et al., J. Neuroscience 2:1129–1149 (1982).

Fifteen um thick slide-mounted brain sections were incubated for 45 minutes in 50 nM Tris-HCl (pH 8.0, 22° C.) containing 1 mg/ml bovine serum albumin (BSA) and 2 nM [$^3$H]DTG. Adjacent sections were incubated with 10 uM haloperidol or 10 uM DTG to measure nonspecific binding. Incubations were terminated by 4×2 minute washes in 10 nM Tris-HCl (pH 7.4, 4° C.) with 1 mg/ml BSA, rapidly dried under a stream of cool air and placed in x-ray cassettes with $^3$H-sensitive film ($^3$H-ultrofilm, LKB). Films were developed 6–8 weeks later (D-19, Kodak).

Example 18

Autoradiographic visualization of [³H]DTG binding

Receptor autoradiography studies on guinea pig and rat brain sections using [³H]DTG showed a low density of specific binding diffusely distributed throughout the gray matter of the rat and guinea pig brain. Superimposed on this homogeneous binding patterns was a heterogeneous distribution of enriched binding in limbic and sensorimotor structures. The pattern of binding was more distinct in the guinea pig than rat. Similar observations for (+)[³H]3-PPP autoradiography have been reported. Largent et al. (1986), supra. Thus, description of [³H]DTG binding was drawn primarily from the guinea pig. In the forebrain, limbic structures moderately to densely labeled by [³H]DTG were the diagonal band of Broca, septum, hypothalamus (especially the paraventricular nucleus), anterodorsal thalamic nucleus and zona incerta. Sensorimotor thalamic nuclei moderately to densely labeled included the thalamic taste relay and reticular nuclei. Other thalamic nuclei labeled were the paraventricular and habenular nuclei. Very dense binding was seen in the choroid plexus. In the cortex dense [³H]DTG labeling occupied layer III/IV of retrospenial piriform, and entorhinal cortices. The rest of the cortex contained a low level of homogeneous binding. The hippocampal formation exhibited discrete binding in the pyramidal granular cell layers. Sensorimotor areas of the midbrain were selectively labeled by [³H]DTG. The oculomotor nucleus, and more caudally, the trochlear nucleus were very densely labeled, and the superior colliculus and red nucleus had moderate levels of binding. Other midbrain nuclei labeled were the dorsal raphe, interpeduncular nucleus, central gray, and the substantia nigra, para compacta. The selective labeling of the para compacta in the guinea pig contrasted with the low to moderate density of labeling present throughout the substantia nigra of the rat. In addition, very dense binding was found in the subcommissural organ. In the hindbrain the locus coeruleus was the most densely labeled nucleus. Sensorimotor nuclei enriched in [³H]DTG binding sites were the trigeminal motor nucleus, nucleus of the facial nerve, nucleus of the solitary tract, dorsal motor nucleus of the vagus, and the hypoglossal nucleus. Moderate to dense binding was also found throughout the gray matter of the cerebellum, and in the pontine reticular nuclei.

Example 19

Drug Specificity of [³H]AZ-DTG binding

The haloperidol-sensitive sigma receptor binds [³H](+)3-[3-hydroxyphenyl]-N-(1-propyl)-piperidine([³H](+)-3-PPP) and [³H]1,3-di-o-tolylguanidine ([³H]DTG), with high affinity. In order to elucidate its structure, photoaffinity labeling of the sigma receptor from guinea pig brain was accomplished using a novel radioactive photolabile derivative of DTG, [³H]-m-azido-1,3-di-o-tolylguanidine ([³H]AZ-DTG). In the dark, [³H]AZ-DTG binds reversibly to sigma sites in brain membranes with high affinity (kd=28 nM). The drug specificity profile of [³H]AZ-DTG binding to brain membranes is identical to that of the prototypical sigma ligands [³H]DTG and [³H](+)-3-PPP. For photoaffinity labeling, membrane suspensions containing protease inhibitors were preincubated in the dark with [³H]AZ-DTG, then filtered and washed over Whatman GF/B glass fiber filters. The filters were then irradiated with long-wavelength UV light for a 15 minute period. Filter-bound proteins were solubilized with 50 mM Tris pH 7.4, 0.1% sodium dodecyl sulfate. Solubilized proteins were subjected to SDS-polyacrylamide gel electrophoresis. Fluorography of the SDS-PAGE gels revealed that [³H]AZ-DTG was selectively incorporated into a 29 kD polypeptide. Labeling of this polypeptide was completely blocked by the sigma ligands DTG, (+)-3-PPP, (+)pentazocine, and haloperidol at a concentration of 10 uM, while labeling was unaffected by morphine, serotonin, dopamine, scopolamine, or GABA at the same concentration. These results represent the first estimate of the size of the binding subunit of the haloperidol-sensitive sigma receptor.

Example 20

Additional sigma receptor binding assays

Sigma receptor binding assays using guinea pig brain membrane homogenates and the radioligands [³H]DTG and (+)[³H]3-PPP were done as previously described (Weber et al., P.N.A.S. (USA) 83:8784–8788 (1986)). Briefly, frozen whole guinea-pig brains (Biotrol, Indianapolis, Ind.) were homogenized in 10 volumes (w/v) of ice-cold 320 mM sucrose using a Brinkman polytron. The homogenate was centrifuged at 1,000×g for 20 minutes at 4° C. The supernatant was centrifuged at 20,000×g for 20 minutes at 4° C. The resulting pellet was resuspended in 10 initial volumes of 50 mM Tris/HCl buffer at pH 7.4 and centrifuged at 20,000×g for 20 minutes at 4° C. The resulting pellet was resuspended in 5 initial volumes ice-cold 50mM Tris/HCl (pH .4), and the final volume was adjusted to yield a protein concentration of 3 mg/ml, as determined by dye-binding protein assay (Biorad) using BSA as the standard. Aliquots of 20-ml were stored at −70° C. until used, with no detectable loss of binding.

For [³H]DTG binding assays, 20-ml aliquots of the frozen membrane suspension were thawed and diluted 1:3 in 50 mM Tris/HCl (pH 7.4). To 12×75 mm polystyrene test tubes were added 0.8 ml of diluted membrane suspension, 0.1 ml of [³H]DTG (46 Ci/mmol; see Weber et al., P.N.A.S (USA) 83:8784–8788 (1986) or (+)[³H3-PPP (NEN, 98 Ci/mmol) to yield a final concentration of 1.4 nM, and 0.1 ml of unlabelled drugs or buffer. The protein concentration in the 1-ml final incubation volume was 800 ug/ml, corresponding to 32 mg of brain tissue (original wet weight) and to a tissue concentration within the linear range for specific binding. Non-specific binding was defined as that remaining in the presence of 10 uM haloperidol. Specific binding constituted >90% of total [³H]DTG binding. Incubations were terminated after 90 minutes at room temperature by addition of 4 ml of ice-cold 50mM Tris/HCl (pH 7.4) and rapid filtration of the membrane suspension through Whatman GF/B glass-fiber filters under vacuum, using a 48-well cell harvester (Brandel, Gaithersburg, MD). The filters were washed 2 times with 4 ml of 50 mM Tris/HCl (pH 7.4). Total filtration and washing time was less than 20 seconds. Each filter was dissolved in 10 ml Cytoscint (Westchem, San Diego, Calif.), and radioactivity was measured by liquid scintillation spectrometry at a counting efficiency of approximately 50%. IC$_{50}$ values were determined by interpolation from displacement-curve plots on semilogarithmic graph paper.

The IC$_{50}$ binding values (nM) are as follows: N,N-di(o-tolyl)guanidine (DTG, 32); N-(2-iodophenyl)-N'-

(adamant-1-yl)guanidine (AdIpG, 6.2±0.7); N-(o-tolyl)-N'-(adamant-1-yl)guanidine (AdTG, 7.6±0.3); N,N'-di(adamant-1-yl)guanidine (DAG, 11.8±3.4); N-(cyclo-hexyl)-N'-(adamant-1-yl)guanidine (AdChG, 12.5±2.2); N-(o-tolyl)-N'-(cyclohexyl)guanidine (13.0±1.0); N,N'-di-(2,6-dimethylphenyl)guanidine (DXG, 90±18); N-(o-tolyl)-N'-(4-amino-2-methylphenyl)guanidine (NH$_2$-DTG, 280±20); N,N'-di(phenyl)guanidine (DPG, 397±21); N-(o-tolyl)-N'-(o-iodophenyl)guanidine (IC$_{50}$=21); N,N'-di-(p-bromo-o-methylphenyl)guanidine (IC$_{50}$=37); N,N'-di-(m-n-propylphenyl)guanidine (IC$_{50}$=36); N-(o-tolyl)-N'-(p-nitro-o-tolyl)guanidine (IC$_{50}$=37); N,N'-di-(1-tetralinyl)guanidine (IC$_{50}$=58); N-(o-tolyl)-N'-(o-xylyl)-guanidine (IC$_{50}$=70); N,N'-di-(o-xylyl)guanidine (IC$_{50}$=90); N,N'-di-(cyclohexyl)guanidine (IC$_{50}$=71); N-(3,5-di-methyl-1-adamantanyl)-N'-(o-tolyl)guanidine (IC$_{50}$=15); N-(3,5-di-methyl-1-adamantanyl)-N'-(o-iodophenyl)guanidine (IC$_{50}$=16); N-(1-adamantyl)-N'-(o-nitrophenyl)guanidine (IC$_{50}$=30); N,N'-di-(endo-2norbornyl)guanidine (IC$_{50}$=16); N-(exo-2-isobornyl)-N'-(o-iodophenyl)guanidine (IC$_{50}$=18); N,N'-di-(exo-2-norbornyl)guanidine (IC$_{50}$=22); N-(exo-2-isobornyl)-N'-(o-tolyl)guanidine (IC$_{50}$=25); N-(o-iodophenyl)-N'-(t-butyl)guanidine (IC$_{50}$=20); N,N'-dibenzylguanidine (IC$_{50}$=90); N-(adamant-1-yl)-N'-(o-isopropylphenyl)-guanidine (IC$_{50}$=24); N-(adamant-2-yl)-N'-(p-iodophenyl)guanidine (IC$_{50}$=2.7); N-(cyclohexyl)-N'(p-bromo-o-tolyl)guanidine (IC$_{50}$=5.5); N-(adamantan-2-yl)-N'-(o-iodophenyl)guanidine (IC$_{50}$=5.2); 2-imino-1,3H-dibenzo[d,f]-[1,3]-diazepine (Bridge-DPG, >10,000); N,N'-di(methyl)guanidine (DMG, >10,000); (+)-3-PPP (76±4); (−)-3-PPP (280±21); (+)-pentazocine (43±2); (−)-pentazocine (135±3); (−)-cyclazocine (2600±210); (−)-SKF10047 (4000±566); haloperidol (5±0.3); BMY 4802 (120±15); rimcazole (1400±100); tiospirone (233±52); perphenazine (42±10); chlorpromazine (1475±265); sulpiride (>10,000); TCP (1100±110); PCP (1050±106); and MK-801 (>10,000). The compound of the invention were found to be potent ligands of sigma receptors as determined by their ability to displace [$^3$H]DTG from sigma receptors in guinea-pig brain homogenates, the most potent being N-adamantan-1-yl-N'-(p-bromo-o-tolyl)guanidine with an IC$_{50}$ of 2.7 nM.

As noted above, the compounds of this invention are useful as anti-hypertensive agents and can be used in the same manner as known antihypertensive agents, e.g., methyldopa, metoprolol tartrate and hydralazine hydrochloride.

Like guanidines generally and N,N'-diphenyl-guanidine specifically, the disubstituted guanidines of this invention, including those of Formulae I and II, are accelerators for the vulcanization of rubbers, e.g., natural rubbers and epoxy group-containing acrylic rubber, and can be used for such purpose in the same manner as N,N'-diphenylguanidine. Thus [$^3$H]-DTG can be incorporated into a vulcanized rubber object, e.g., a tire tread, and rate of loss of rubber therefrom by water can be monitored by rate of loss of radioactivity.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of treating hypertension which comprises administering to a hypertensive person, in an amount effective to ameliorate the hypertensive state, an N,N'-disubstituted guanidine of the following formula

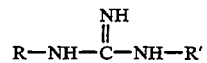

wherein R and R' each is substituted or unsubstituted alkyl of at least 4 carbon atoms, a cycloalkyl group of 3 to 12 carbon atoms or a carbocyclic aryl of at least 6 carbon atoms, wherein at least one of said R or R' is adamantyl.

2. The method of claim 1 wherein R and R' are independently adamantyl, cyclohexyl or a monocyclic carbocyclic aryl of at least 6 carbon atoms.

3. The method of claim 2 wherein one or both of said R or R' group is substituted by alkyl of 1–8 carbon atoms, hydroxyalkyl of 1–8 carbon atoms, halo, hydroxy, nitro, azido, cyano, isocyanato, amino, lower-alkylamino, di-lower-alkyl amino, trifluoromethyl, alkoxy of 1–8 carbon atoms, alkanoyloxy of 1–8 carbon atoms, amido, or carbamido.

4. The method of claim 1 wherein R and R' are independently phenyl or adamantyl.

5. The method of claim 4 wherein one or both of said R or R' group is substituted by alkyl of 1–8 carbon atoms, hydroxyalkyl of 1–8 carbon atoms, halo, hydroxy, nitro, azido, cyano, isocyanato, amino, lower-alkylamino di-lower-alkyl amino, trifluoromethyl, alkoxy of 1–8 carbon atoms, alkanoyloxy of 1–8 carbon atoms, amido, or carbamido.

6. The method of claim 1 wherein R is adamantyl and R' is ortho-substituted phenyl.

7. The method of claim 1 wherein at least one of R and R' is o-tolyl.

8. The method of claim 1 wherein the guanidine is N-(1-adamantyl)-N'-(o-tolyl)guanidine.

9. The method of claim 1 wherein the N,N'-disubstituted guanidine is selected from the group consisting of N,N'-dibutylguanidine; N,N'-diphenylguanidine; N,N'-di-o-tolylguanidine; N,N'-di-(2-methyl-4 -bromophenyl)guanidine; N,N'-di-(2-methyl-4-iodophenyl)-guanidine; N-(2-methyl-4-azidophenyl)-N'-( 2-methylphenyl)-guanidine; N,N'-diadamantyl-guanidine; N-adamantyl-N'-(2-methylphenyl)guanidine; N-(2-iodophenyl)-N'-(methylphenyl)guanidine; N-(2-methyl-4-nitrophenyl)-N'-(2-methylphenyl)guanidine; N,N'-di(2,6-dimethylphenyl)guanidine; N-(2,6-dimethylphenyl)-N'-(2-methylphenyl)guanidine; N-(adamantyl)-N'-(cyclohexyl)guanidine; N,N'-di(cyclohexyl)guanidine; N-(2-iodophenyl)-N'-(adamantyl)guanidine; N-(2-methylphenyl)-N'-cyclohexyl-guanidine; N-adamantyl-N'-phenyl-guanidine; N,N'-di(p-bromo-o-tolyl)guanidine; N-(o-tolyl)-N'-(p-nitro-o-tolyl)guanidine; N-(o-tolyl)-N'-(o-xylyl)guanidine; N,N'-di-(o-xylyl)guanidine; N-(2-adamantyl)-N'-(o-iodophenyl)guanidine, N-(1-adamantyl)-N'-(o-tolyl)guanidine, N-(3,5-dimethyl-1-adamantyl)-N'(o-tolyl)guanidine; N-(3,5-dimethyl-1-adamantyl)-N'-(o-iodophenyl)guanidine; N-(1-adamantyl)-N'-(o-nitrophenyl)guanidine; N-(o-iodophenyl)-N'-(t-butyl)guanidine; N,N'-dibenzylguanidine; N-(1-adamantyl)-N'-(o-isopropylphenyl)guanidine; N-(1- adamantyl)-N'-(p-bromo-o-tolyl)guanidine; N-(cyclohexyl)-N'-(p-bromo-o-tolyl)guanidine; N-(2-adamantyl)-N'-(o-iodophenyl)guanidine; N,N'-di(o-methylbenzyl)guanidine and N,N'-di(1-adamantanylmethyl)guanidine.

10. The method of claim 1 wherein a pharmaceutical composition comprising a pharmaceutically acceptable carrier and the N,N'-disubstituted guanidine is administered to the hypertensive person.

11. The method of claim 1 wherein the guanidine is administered as a water-soluble salt.

12. The method of claim 1 wherein R or R' is substituted in 1-3 positions.

13. The method of claim 1 wherein R is o-tolyl and R' is adamantyl.

14. A method of treating hypertension which comprises administering to a hypertensive person, in an amount effective to ameliorate the hypertensive state, a compound selected from the group consisting of (+)-N-(2-exonorbornyl)-N'-(2-iodophenyl)guanidine; (−)-N-(2-exonorbornyl)-N'-(2-iodophenyl)guanidine; (+)-N-(2-endonorbornyl)-N'-(2-iodophenyl)guanidine; (−)-N-(2-endonorbornyl)-N'-(2-iodophenyl)guanidine; (+)-N-(2-endonorbornyl)-N'-(o-tolyl)guanidine; (+)-N,N'-di-(endo-2-norbornyl)guanidine; (−)-N,N'-di-(endo-2-norbornyl)guanidine; (+)-N-(exo-2-isobornyl)-N'-(o-iodophenyl)guanidine; (−)-N-(exo-2-isobornyl)-N'-(o-iodophenyl)guanidine; (+)-N,N'-di-(exo-2-norbornyl)guanidine; (−)-N,N'-di-(exo-2-norbornyl)guanidine; (+)-N-(exo-2-isobornyl)-N'-(o-tolyl)guanidine; N,N'-di-(1-tetralinyl)guanidine; and (−)-N-(exo-2-isobornyl)-N'-(o-tolyl)guanidine.

15. A method of treating hypertension which comprises administering to a hypertensive person, in an amount effective to ameliorate the hypertensive state, a compound having the formula:

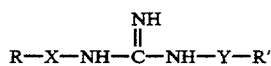

wherein
X and Y are independently branched or straight chain $C_1$–$C_{12}$ alkylene or a branched or straight chain $C_2$–$C_{12}$ unsaturated alkylene or wherein one of X and Y is a single bond;
R and R' are independently hydrogen, a cycloalkyl group of at least 3 carbon atoms, a carbocyclic aryl group of at least 6 carbon atoms, aralkyl of at least 6 carbon atoms and containing 1-3 separate or fused rings, with at least one of said R or R' being adamantyl, and wherein each of R and R' may be substituted in 1-3 positions.

16. The method of claim 15 wherein R and R' are each independently adamantyl, cyclohexyl or a monocyclic carbocyclic aryl of at least 6 carbon atoms.

17. The method of claim 15 wherein R and R' are independently phenyl or adamantyl.

18. The method of claim 17 wherein said R or R' group is substituted by alkyl of 1-8 carbon atoms, hydroxyalkyl of 1-8 carbon atoms, halo, hydroxy, nitro, azido, cyano, isocyanto, amino, lower-alkylamino di-lower-alkyl amino, trifluoromethyl, alkoxy of 1-8 carbon atoms, alkanoyloxy of 1-8 carbon atoms, amido, or carbamido.

19. The method of claim 15 wherein X and Y are $C_1$–$C_4$ alkylene groups.

20. A method of treating hypertension which comprises administering to a hypertensive person, in an amount effective to ameliorate the hypertensive state, a compound of the formula

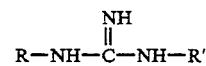

wherein R and R' are an alkyl group of at least 3 carbon atoms, a cycloalkyl group of at least 3 carbon atoms, a carbocyclic aryl group of at least 6 carbon atoms, alkaryl or aralkyl of at least 6 carbon atoms and containing 1-3 separate of or fused rings, and wherein each of R and R' may be substituted in 1-3 positions, with at least one of said R or R' being adamantyl.

21. A method of treating hypertension which comprises administering to a hypertensive person, in an amount effective to ameliorate the hypertensive state, N-(1-adamantyl)-N'-(o-tolyl)guanidine.

22. The method of claim 21 wherein N-(1-adamantyl)-N'-(o-tolyl)guanidine is administered as a water-soluble salt.

23. The method of claim 21 wherein a pharmaceutical composition comprising a pharmaceutically acceptable carrier and N-(1-adamantyl)-N'-(o-tolyl)guanidine is administered to the hypertensive person.

24. The method of claim 21 wherein a pharmaceutical composition comprising a pharmaceutically acceptable carrier and a water soluble salt of N-(1-adamantyl)-N'-(o-tolyl)guanidine is administered to the hypertensive person.

25. The method of claim 15 wherein the compound is administered as a water-soluble salt.

26. The method of claim 20 wherein the compound is administered as a water-soluble salt.

* * * * *